US 6,712,762 B1

(12) United States Patent
Lichter et al.

(10) Patent No.: US 6,712,762 B1
(45) Date of Patent: *Mar. 30, 2004

(54) PERSONAL COMPUTER CARD FOR COLLECTION OF REAL-TIME BIOLOGICAL DATA

(75) Inventors: Patrick A. Lichter, Plymouth, MN (US); Spencer J. Lien, Medina, MN (US)

(73) Assignee: ORS Diagnostic, LLC, Plymouth, MN (US)

( * ) Notice: Subject to any disclaimer, the term of this patent is extended or adjusted under 35 U.S.C. 154(b) by 567 days.

This patent is subject to a terminal disclaimer.

(21) Appl. No.: 09/666,878

(22) Filed: Sep. 20, 2000

Related U.S. Application Data

(63) Continuation of application No. 09/173,059, filed on Oct. 15, 1998, now Pat. No. 6,159,147, which is a continuation-in-part of application No. 08/810,632, filed on Feb. 28, 1997, now Pat. No. 5,827,179.

(51) Int. Cl.[7] .................................................. A61B 5/00
(52) U.S. Cl. ....................... 600/300; 600/509; 128/920
(58) Field of Search ................................. 600/300, 323, 600/538, 544, 546, 481, 508, 509; 128/920

(56) References Cited

U.S. PATENT DOCUMENTS

| 3,921,147 A | 11/1975 | Fuhr et al. |
| 4,356,475 A | 10/1982 | Neumann et al. |
| 4,751,931 A | * 6/1988 | Briller et al. ................ 600/509 |
| 4,905,709 A | 3/1990 | Bieganski et al. |
| 5,275,159 A | 1/1994 | Griebel |
| 5,305,202 A | 4/1994 | Gallant et al. |
| 5,307,263 A | 4/1994 | Brown |
| 5,501,231 A | 3/1996 | Kaish |
| 5,518,002 A | 5/1996 | Wolf et al. |
| 5,549,115 A | 8/1996 | Morgan et al. |
| 5,562,101 A | 10/1996 | Hankinson et al. |
| 5,564,432 A | 10/1996 | Thomson |
| 5,609,158 A | 3/1997 | Chan |
| 5,623,925 A | 4/1997 | Swenson et al. |
| 5,661,538 A | 8/1997 | Carter |
| 5,687,717 A | 11/1997 | Halpern et al. |
| 5,701,894 A | 12/1997 | Cherry et al. |
| 5,804,971 A | 9/1998 | Cumming et al. |
| 5,827,179 A | 10/1998 | Lichter et al. |
| 6,159,147 A | * 12/2000 | Lichter et al. ............... 600/300 |

FOREIGN PATENT DOCUMENTS

EP 94117681.0 5/1995

OTHER PUBLICATIONS

Steven L. Honor, William M. Holls II, and Paul B. Crilly, A Real–tme System for Monitoring a Non–invasive and Invasive FECG, Oct. 18–21, 1994, 204–209.

(List continued on next page.)

Primary Examiner—Eric F. Winakur
(74) Attorney, Agent, or Firm—Kinney & Lange, P.A.

(57) ABSTRACT

A real-time biological data processing PC card is lightweight, cost effective, and portable. The real-time biological data processing PC card is capable of converting a host personal computer system into a powerful diagnostic instrument. Each real-time biological data processing PC card is adapted to input and process biological data from one or more biological data sensors, and is interchangeable with other real-time biological data processing PC cards. A practitioner having three different real-time biological data processing PC cards, for example, each one corresponding to a different biological data collection device, effectively carries three full-sized, powerful diagnostic instruments. The full resources of a host personal computer can be utilized and converted into a powerful diagnostic instrument, for each biological data collection device, by the insertion of one of the real-time biological data processing PC cards.

36 Claims, 26 Drawing Sheets

OTHER PUBLICATIONS

NASA Tech Briefs, The Latest Computer Hardware, vol. 20 No. 6, Jun. 1996, 92.

Richard F. Ferraro, LP–Pac Q Signal–Average ECG in a Package, Jan. 29, 2003, 1,2,31,32.

Lorenzo Basano, et al., An Instrument for real–time spectral estimation of heart rate variability signals, 1995, 229–236.

About Nasiff Associates, Apr. 16, 2003, 1.

Nasiff Associates, Cardio–Card Resting Interpretive PC ECG, Apr. 18, 2003, 1–4.

Nasiff Associates, Vitals—ECG,Blood Pressure, SpO2, Temperature, Apr. 28, 2003, 1–4.

Nasiff Associates, Stress ECG, Apr. 28, 2003, 1–4.

R.P.K.Ford, et al., HomeLog: Long–term recording of infant temperature, respiratory and cardiac signals in the home environment, J. Paediatr. Child Health , Suppl. 1, 1992, S26–32.

Y.Ziya Ider and Ali Oto, PC Based High Resolution ECG System, 1991EEE, 665–668.

N. Pulido, et al., ECG Processing System To Integrate Data To Aid In Secondary Prevention Involving Post–Infarction Risk Patients, 1997 IEEE, 733–734.

Cheryl Ajluni, The World Of Sensors Bristles With Activity, Electronic Design/Sep. 5, 1995, 85–88.

DAQCard–700 User Manual, Multifunction I/O Board for the PCMCIA Bus, Jan. 1996 Edition.

Warren D. Smith, et al., LabVIEW Facilitates Interdisciplinary Team Projects in Graduate Biomedical Engineering Courses, Sep. 9, 1999, 1–10.

G. Premalatha and C. Eswaran, Personal computer based cardiac monitor, vol. 16 No. 6 1992, 311–320.

Wolfgang Grossbach, Measuring the ECG Signal with a Mixed Analog–Digital Application–Specific IC, Oct. 1991Hewlett–Packard Journal, 21–24.

Damjan Zazula, et al., Computer–assisted exercise ECG analysis: real–time scheduling within MS–DOS on PCs, Microprocessors and Microsystems vol. 18 No. 9, Nov. 1994, 523–535.

Chi C. Chen, et al., A Mobile Real–Time Bioengineering Front End System, Biomedical Sciences Instrumentation vol. 29, 427–434.

J. Jossinet, et al., A Computerized Bioelectrical Cardiac Monitor, Comput. Biol. Med vol. 20, No. 4, 1990, 253–260.

Cor. J. Kalkman, MD, PhD, LabVIEW: A Software System for Data Acquisition, Data Analysis, and Instrument Control, Journal of Clinical Monitoring, vol. 11, No. 1, Jan. 1995, 51–58.

J.S. Sahambi, et al., DSP Based Enhanced Data Acquisition System, vol. 31, Apr. 11, 1995, 247–250.

Say Yes to the BIOPAC MP100WS, IEEE Engineering In Medicine And Biology Magazine, vol. 10, No. 3, Sep. 1991.

The MP100WS Beats All Competition!, IEEE Engineering In Medicine And Biology Magazine, vol. 12, No. 4, Dec. 1993, Circle No. 6.

Stephen J. Bigelow, PC Cards, Electronics Now 66 31–6 Jun. 1995, 1–8.

Caren D. Potter, PCMCIA Cards, The Scientist, Aug. 21, 1995, 1–5.

Allen E. Tracht, Adapting laptops to data acquisition, IEEE Spectrum Oct. 1993, 45–47.

John Novellino, Changing technology boosts data acquisition, Electronic Design, Test & Measurement Special Editorial Feature, Jun. 26, 1995, 141, 142, 144.

Edward W. Bassett, PC Data Acquisition Now Smaller, Portable, Jul. 1994 INTECH, 36–37.

Bert Haskell, Portable Electronics Packaging Technologies, IEEE Micro vol. 14, No. 5, 1994 IEEE, 72–78.

Tom DeSantis, Data Acquisition Plug s Into Notebook PCs, INTECH Applying Technology, vol. 40, No. 7, Jul. 1993, 50–51.

David Potter, Portable PC–Based Data Acquisition—An Overview, 15–21.

Sensors Magazine—1995 Article Index, 1–4.

Electronic Engineering Times, MN—Minitex Statewide Database Access Program, Article 6, May 1, 1995, 1–2.

The Biomch–L Newsgroup, Biomch–L, 1–2 and 1–9.

Search Results: Biomch–L Archives, Feb. 13, 2003, 1–2.

Data Logger Summary, Feb. 13, 2002, 1–4.

Technical help, Feb. 13, 2003, 1 and 1–3.

Portable A/D System—Responses, Feb. 13, 2003, 1–9.

Portable A/D Systems, Feb. 13, 2003, 1–2.

Summary: Portable data recorders, Feb. 13, 2003, 1–9.

Flexible science tool (Virtual Instruments), Feb. 13, 2003, 1–5.

Advance for Respiratory Managers Magazine, Advertisement Now You Can Enjoy The Benefits Of Spirometry Testing, QRS, 8/96.

Technology Providers, Microsoft Press Release—Comdex Trade Show in Las Vegas, 11/96.

* cited by examiner

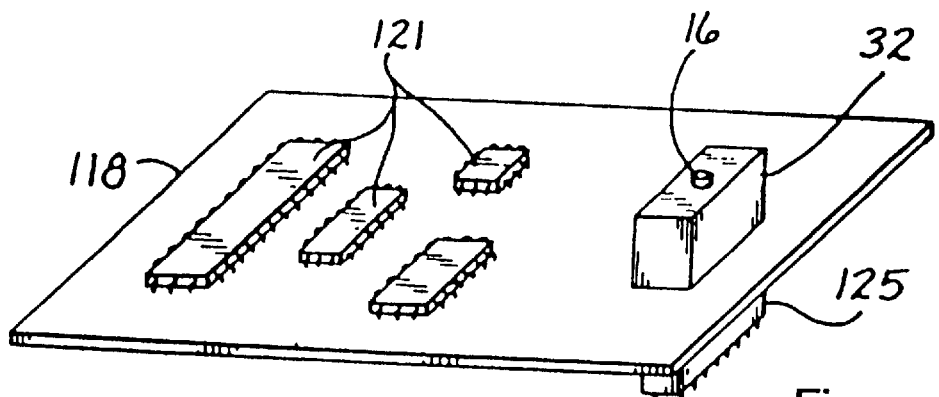
Figure 6a
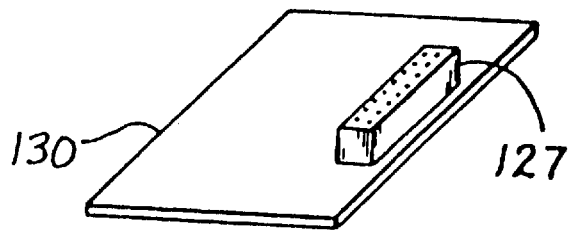
Figure 6b
Figure 7
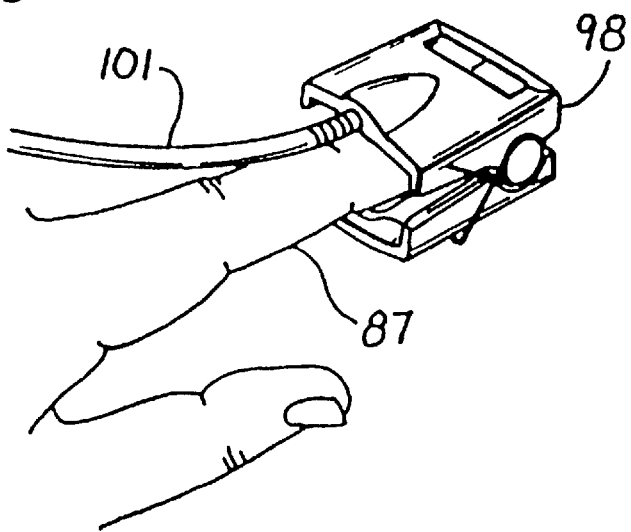

PERSONAL COMPUTER CARD FOR COLLECTION OF REAL-TIME BIOLOGICAL DATA

This application is a continuation of U.S. application Ser. No. 09/173,059, filed on Oct. 15, 1998, entitled PERSONAL COMPUTER CARD FOR COLLECTION OF REAL-TIME BIOLOGICAL DATA, now U.S. Pat. No. 6,159,147, which is a continuation-in-part of U.S. application Ser. No. 08/810,632, filed Feb. 28, 1997 entitled PERSONAL COMPUTER CARD FOR COLLECTION OF REAL-TIME BIOLOGICAL DATA, now U.S. Pat. No. 5,827,179, both of which are commonly assigned and the contents of which are expressly incorporated herein by reference.

BACKGROUND OF THE INVENTION

1. Field of the Invention

The present invention relates generally to personal computer (PC) cards and, more particularly, to PC cards for use in combination with personal computers for collecting biological data on a real-time basis.

2. Description of Related Art

The United States health care system is currently in the midst of a transformation away from specialized medicine toward a more cost-conscious, primary-care oriented system. Devices having cost-effective means for diagnosing and monitoring patients are expected to gain prominence in the market place. Many current data acquisition devices exist in the medical industry, but few, if any, of these devices are economical, extremely lightweight and portable, accurate, versatile, and interchangeable with other biological data collection devices.

One prior art device, manufactured by the assignee of the present application, incorporates a diagnostic box which is adapted to interface with a serial port of a personal computer. This diagnostic box is manufactured with a relatively expensive housing, having a size approximately equal to that of a book, an alternating current (AC) chord and power adapter, a serial port cable, a microprocessor, and other hardware elements.

The diagnostic box allows a user to perform real-time spirometry operations, while harnessing the PC compute's display, keyboard, printer, and other items. The PC computer display instructs the user with selectable patient incentives, and user-customized reports can be generated. The display of the personal computer can be configured to display volume-versus-time and flow-versus-volume curves. Additionally, parameters such as maximum exhale volume, maximum inhale volume and maximum flow rate can be computed and displayed on the personal computer display.

Data acquisition cards have existed in the prior art for transferring electrical signals from a data sensor through the data acquisition card and into a personal computer. These data acquisitions cards have been configured into Personal Computer Memory Card International Association (PCMCIA) cards.

Prior art data acquisition cards are often configured to measure potential signals ranging from zero to ten volts, and are often configured with twelve bit accuracy. A typical prior art data acquisition card may comprise a 30 pin connector and a cable, which is connected to a connector board. The connector board allows a user to hook up various signals thereto. In addition to the relatively high-voltage signal range (zero to ten volts), low-accuracy (e.g. twelve bits), extra hardware (30 pin connector, cable, and a connector board), and additional optional hardware, these prior art data acquisition cards are configured with a plurality of inputs and outputs and, further, are not adapted to convert a personal computer into a powerful biological data signal collecting, processing, and monitoring system.

Prior art data acquisition cards are not adapted for performing spirometry collection and analysis, since these cards are not equipped with pressure transducers for converting pressure signals into electrical signals. Even if these prior art data acquisition cards were equipped with pressure transducers, the cards would not be equipped with high-precision low-voltage signal collection and conditioning circuitry. A prior art data acquisition card, additionally, would not be suitable for other biological data collection and processing purposes, such as Electrocardiography (ECG) biological data collection, since these prior art data acquisition cards are not equipped with any insulating means for insulating a patient from potential shock, which may be delivered from the data acquisition card to the patient.

Another prior art device is disclosed in U.S. Pat. No. 5,549,115 to Morgan et al. The Morgan et al. patent generally discloses a PCMCIA format card which is adapted to perform as a data storage device, similarly to a floppy disc storage device. The PCMCIA format cart of Morgan et al. is equipped with a real-time clock for providing time and date data to the host system, in order to synchronize the host system time with the time of which the data was actually acquired. The PCMCIA format card of Morgan et al. does not provide any means for real-time data collection and processing and, accordingly, is not suitable for converting a host PC computer into a real-time biological data signal collection, processing, and monitoring-system. The system of the Morgan et al. patent requires a separate dedicated computer device for acquiring the data, and-a separate personal computer device for processing the data at a later time.

U.S. Pat. No. 5,546,432 to Thomson discloses a spirometer which includes control electronics located remotely from a hand-held housing. Communication between the hand-held housing, which includes an analog-to-digital (A/D) converter and an amplifier, occurs through a cable. A dedicated microprocessor including a simple keyboard structured and adapted specifically to control the operation of a spirometer is included in the Thomson device. The handle-shaped housing of the Thomson patent is quite different from a PC card.

A need exists in the prior art for real-time biological data signal collecting, processing, and monitoring systems, which are extremely lightweight and portable. The prior art has not introduced any cost-effective PC card, which is adapted to convert a host personal computer into any of a variety of real-time data collecting and processing systems.

SUMMARY OF THE INVENTION

The real-time biological data processing PC card of the present invention is very lightweight, cost effective, and portable. The real-time biological data processing PC card of the present invention is capable of converting a host personal computer system into a powerful diagnostic instrument. Each real-time biological data processing PC card is adapted to input and process biological data from one or more biological data sensors, and is interchangeable with other real-time biological data processing PC cards. A practitioner having three different real-time biological data processing PC cards, each one corresponding to a different biological data collection device, effectively carries three full-sized, powerful diagnostic instruments. The full resources of a host personal computer may be utilized and converted into a powerful diagnostic instrument, for each biological data collection device, by the insertion of one of the real-time biological data processing PC cards.

A portable computer card for collecting biological data, according to the present invention, includes a pressure transducer adapted to receive an air pressure from an air tube and to convert the air pressure into an electrical signal. The portable computer card includes an analog-to-digital converter adapted to receive and digitize the electrical signal, and a portable computer card interface adapted to provide an interface between the portable computer card and a host microprocessor system. The portable computer card interface may comprise a PCMCIA card interface. An amplifier, which is adapted to receive and amplify the electrical signal from the pressure transducer, is disposed between the pressure transducer and the analog-to-digital converter. The amplified electrical signal is related to the air pressure. The portable computer card further includes a housing, which is adapted for holding the pressure transducer, the amplifier, the analog-to-digital converter, and the portable computer card interface. A pressure input port is disposed on the housing. This pressure input port is in fluid communication with the pressure transducer and is adapted to receive an air pressure from an air tube. The portable computer card further includes a flexible air passageway, which is integrally connected to the housing, and which is adapted to supply an air pressure to the pressure input port.

According to still another aspect of the present invention, a portable biological data collection device includes a portable computer card housing, a biological data receiver, signal conditioning circuitry, and a portable computer card interface. The biological data receiver is adapted to receive biological data and to output the biological data, and the signal conditioning circuitry is adapted to receive the biological data from the biological data receiver and to convert the biological data into digitized biological data. The portable computer card interface is disposed within the portable computer card housing, and is adapted to communicate with a host computer to relay the digitized biological data to the host computer on a real-time basis as the biological data is converted by the signal conditioning circuitry.

The biological data receiver can be adapted to receive biological data from a pulse oximetry sensor, which is located externally of the portable biological data collection device. The biological data receiver can further be adapted to receive biological data from an ECG sensor. The biological data sensor is adapted to output low-amplitude signals on an order of one millivolt. The digitized data from the analog-to-digital converter preferably has a resolution greater than 12 bits and, preferably, has a resolution of 16 bits. The biological data sensor may further include a spirometer air tube.

According to another aspect of the present invention, a host computer is configurable among a plurality of biological data collection device modes. The host computer includes a portable computer card slot adapted to receive a portable computer card therein, a portable computer card interface adapted to communicate with a portable computer card inserted into the portable computer card slot, a microprocessor, a data bus, and input means for receiving designation data from a portable computer card within the portable computer card slot. The portable computer card interface is adapted to receive digitized biological data from a portable computer card inserted into the portable computer card slot, and the input means is operatively connected to the microprocessor. The designation data is indicative of a type of digitized biological data from a portable computer card inserted into the portable computer card slot. The designation data may comprise either a first identifier for indicating that the digitized biological data should be interpreted by the microprocessor as spirometer-pressure data or a second identifier indicating that the digitized biological data should be interpreted by the microprocessor as pulse oximetry electrical data. The host computer includes configuration means for configuring the host computer into a real-time spirometer-pressure data collecting and analyzing device upon receipt of the first identifier, and for configuring the host computer into a real-time pulse oximetry electrical data collecting and analyzing device upon receipt of the second identifier. The host computer may also be configured into an ECG data collection device mode, upon receipt of a third identifier from the input means. Additionally, the host computer may be configured among various other biological data collection device modes, upon receipt of additional identifiers.

According to yet another aspect of the present invention, a combination of a plurality of interchangeable biological data portable computer cards includes a spirometer portable computer card and a pulse oximetry portable computer card. The spirometer portable computer card and the pulse oximetry portable computer card are both insertable into a personal computer system, and are interchangeable. The spirometer portable computer card is adapted to convert the host computer into a spirometer data collecting and analyzing device, and the pulse oximetry portable computer card is adapted to convert the host computer into a pulse oximetry data collecting and analyzing device. The combination of interchangeable biological data portable computer cards may further include an ECG portable card, as well as other computer cards, each being adapted to convert the host personal computer into a different type of biological data collecting and analyzing device.

According to another aspect of the present invention, a portable computer card for delivering biological data to a host computer includes a portable computer card housing, at least one conductor connected to the portable computer card housing, an amplifier operatively connected to the at least one conductor, a power source operatively connected to the amplifier, and insulating means for providing electrical insulation between the power source and the conductor. The conductor is adapted to collect biological data from a patient, and the amplifier is adapted to receive the biological data and to output an amplified signal. The insulating means may comprise an optical translator, and can be positioned between the conductor and the amplifier. The portable computer card further includes an analog-to-digital converter for digitizing the amplified signal, and a portable computer card interface for providing a communication link between the portable computer card and a host personal computer system. The portable computer card interface is adapted to relay the digitized amplified signal to the host computer on a real-time basis, as biological data is collected from a patient. The power source comprises a conductor, which is adapted for receiving power from the host personal computer.

The present invention, together with additional features and advantages thereof, may best be understood by reference to the following description taken in connection with the accompanying illustrative drawings.

BRIEF DESCRIPTION OF THE DRAWINGS

FIG. 1a illustrates an end view of the real-time biological data processing PC card of FIG. 1, taken from the direction of the line 1a—1a;

FIG. 6a illustrates a simplified perspective view of the main circuit board of the real-time biological data processing PC card according to the present invention;

FIG. 6b illustrates a pulse oximeter module circuit board according to the present invention;

FIG. 7 illustrates an articulated finger clip sensor according to the present invention;

DETAILED DESCRIPTION OF THE PRESENTLY PREFERRED EMBODIMENTS

Figure 1A:
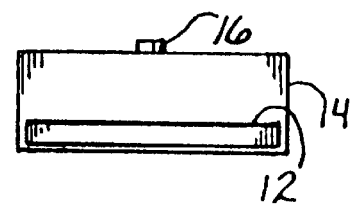
Figure 1B:
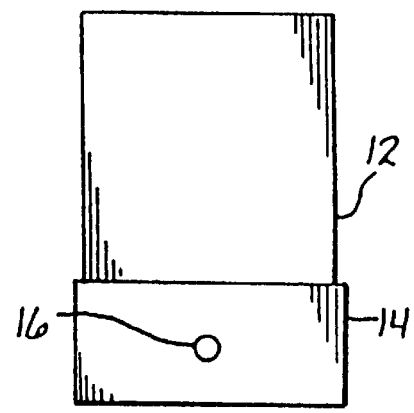
FIG. 1b illustrates a top planar view of the real-time biological data processing PC card, without the air tube connection.
Figure 1:
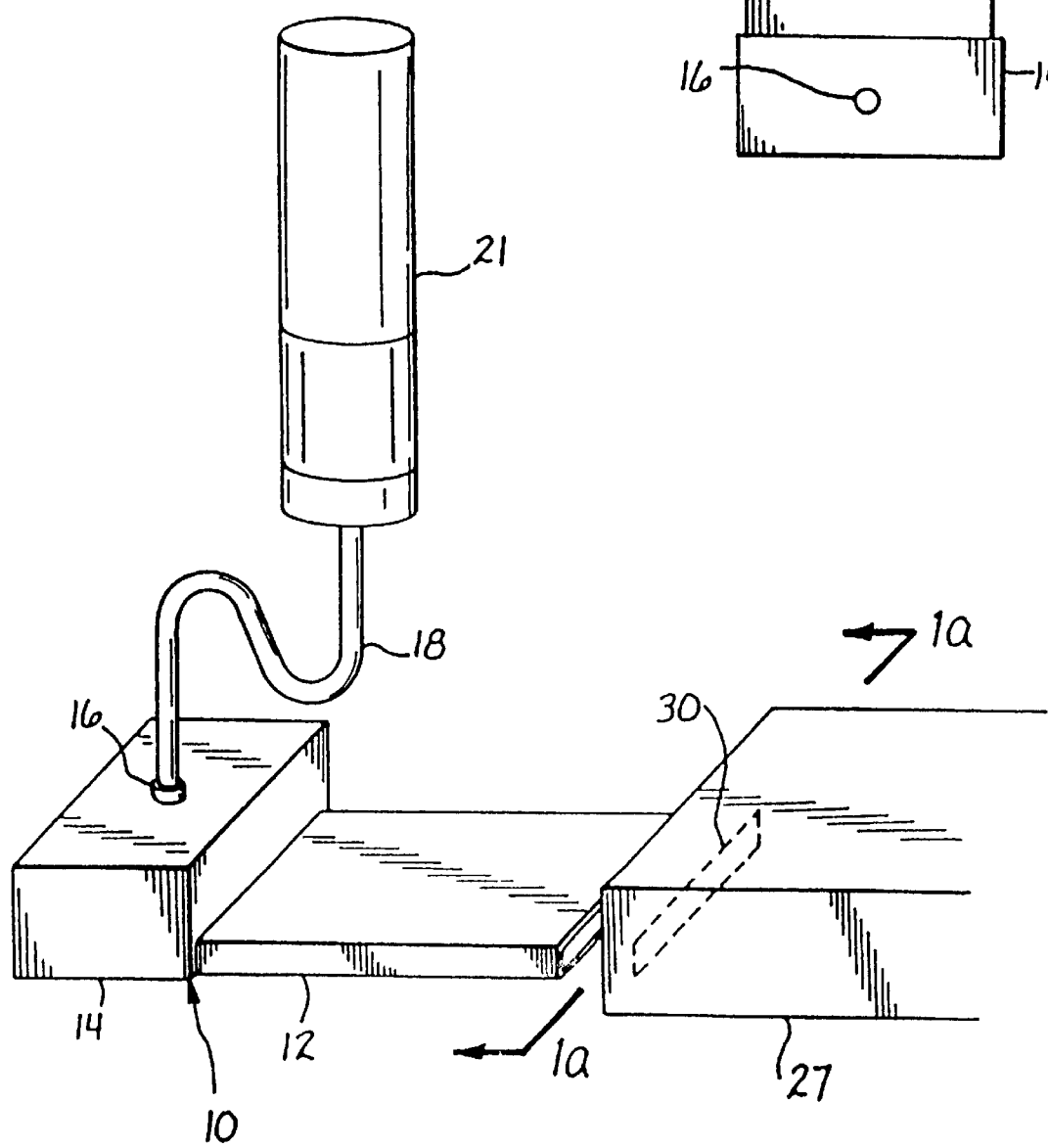
FIG. 1 illustrates a real-time biological data processing PC card according to the present invention.

Turning to FIG. 1, a real-time biological data processing PC card 10 is illustrated having a Personal Computer Memory Card International Association (PCMCIA) format housing 12 and a pressure transducer housing 14. The pressure transducer housing 14 preferably comprises a pressure input port 16, which is adapted to removably accommodate a flexible air passageway 18. A disposable spirometry mouthpiece 21 is attached to one end of the flexible air passageway 18, and a connector is attached to the other end of the flexible air passageway 18. As presently embodied, the connector comprises a truncated, conical shape which is adapted for matingly fitting within the pressure input port 16. After a user breaths into the disposable spirometry mouthpiece 21, the flexible air passageway 18 and the disposable spirometry mouthpiece 21 may be removed from the pressure input port 16, and discarded. In the below description and claims, the term "spirometry" is intended to encompass not only the general meaning of the word, but also to broadly encompass any other pulmonary function which can be detected by measuring air flow, pressure or volume.

The PCMCIA format housing 12 of the real-time biological data processing PC card 10 is preferably configured to conform with PCMCIA dimensional standards. As presently preferred, the PCMCIA format housing has a width of approximately 2.95 inches. The PCMCIA format housing 12 preferably comprises a length of approximately 3.40 inches. The pressure transducer housing 14, according to the presently preferred embodiment, has dimensions which are larger than PCMCIA conventions permit. As presently embodied, the pressure transducer housing 14 comprises a height of approximately 1 inch. These enlarged dimensions of the pressure transducer housing 14 facilitate placement of biological sensor circuitry, such as, for example, a pressure transducer.

FIG. 1a illustrates an end view of the real-time biological data processing PC card 10, taken from a view along the line 1a—1a of FIG. 1, and FIG. 1b illustrates a top-planar view of the real-time biological data processing PC card 10. A host personal computer 27 comprises a PCMCIA format slot 30, which is sized and dimensioned according to PCMCIA dimensional standards, in order to facilitate insertion of the PCMCIA format housing 12 therein.

Figure 2:
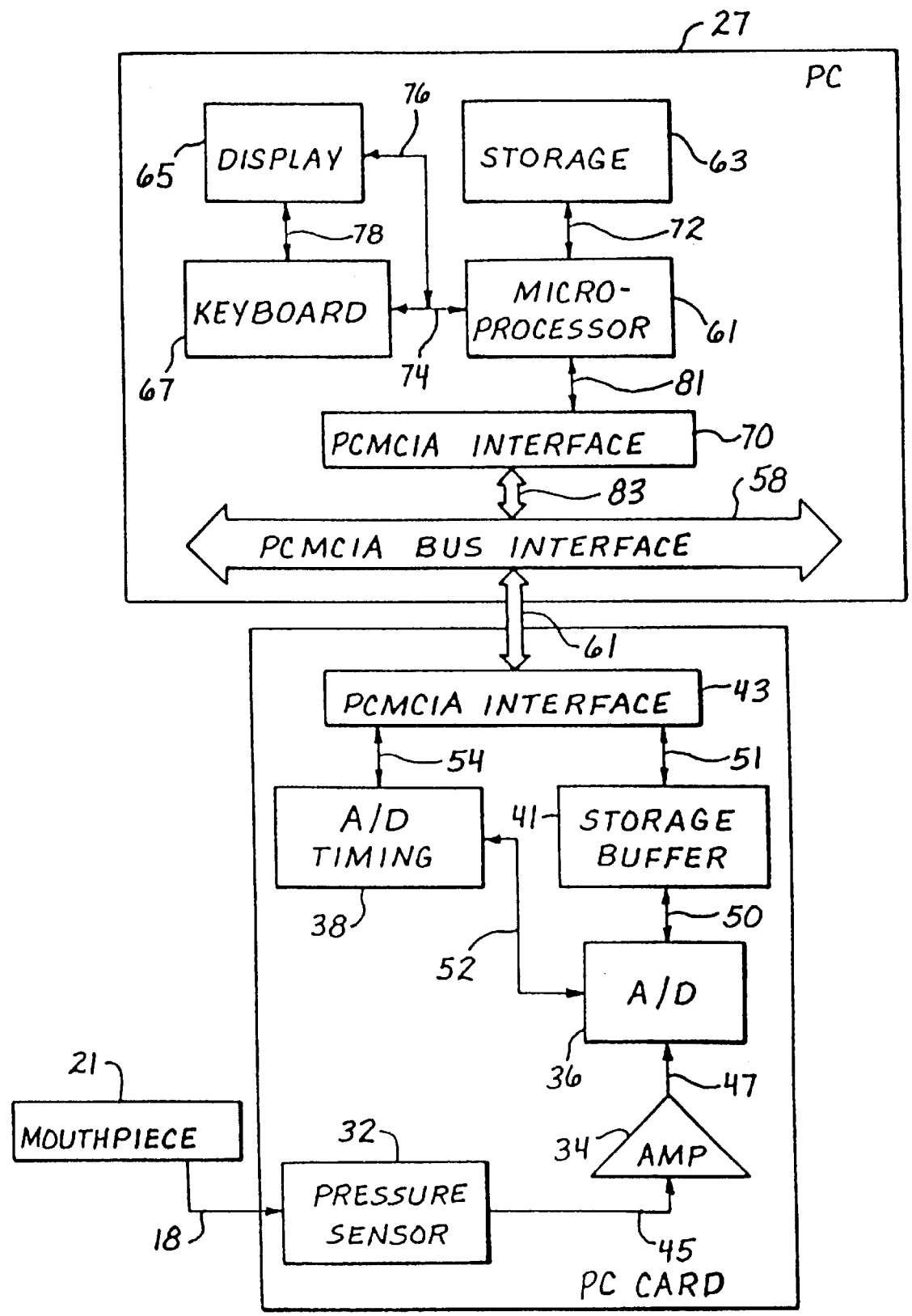
FIG. 2 illustrates a schematic block diagram of the circuitry of the real-time biological data processing PC card and a host personal computer system, according to the present invention.

FIG. 2 illustrates a schematic block diagram of components associated with the real-time biological data processing PC card 10 and the host personal computer 27. The real-time biological data processing PC card 10 comprises a pressure sensor 32, an amplifier 34, an analog-to-digital converter 36, an analog-to-digital timing circuit 38, a storage buffer 41, and a PCMCIA interface 43. The flexible air passageway 18 connects the disposable spirometry mouthpiece 21 to the pressure sensor 32, and a conductor path 45 connects the pressure sensor 32 to the amplifier 34. The amplifier 34 is connected to the analog-to-digital converter 36 via a conductor path 47, and the analog-to-digital converter 36 is connected to the storage buffer 41 via a conductor path 50. A conductor path 52 connects the analog-to-digital converter 36 to the analog-to-digital timing circuit 38, and a conductor path 54 connects the analog-to-digital timing circuit 38 to the PCMCIA interface 43. The storage buffer 41 is connected to the PCMCIA interface 43 via a conductor path 51. Upon insertion of the real-time biological data processing PC card 10 into the PCMCIA format slot 30, the PCMCIA interface 43 is connected to a PCMCIA bus interface 58 via a bus 61.

The host personal computer 27 comprises a microprocessor 61, a storage 63, a display 65, a keyboard 67, and a PCMCIA interface 70. The host personal computer 27, of course, may comprise other components which are not shown in FIG. 2. The microprocessor 61 is connected to the storage 63 via a bus 72, and is connected to the keyboard 67 via a bus 74. A bus 76 connects the display 65 to the bus 74, and a bus 78 connects the display 65 to the keyboard 67. The microprocessor 61 is connected to the PCMCIA interface 70 via a bus 81, and the PCMCIA interface 70 is connected to the PCMCIA bus interface 58 via a bus 83.

When the real-time biological data processing PC card 10 and the host personal computer 27 are configured as shown in FIG. 2, communication between the devices and 27 can occur via standardized PCMCIA protocols. The PCMCIA Developer's Guide—2nd Edition, published by Sycard Technology in 1994, the contents of which are expressly incorporated herein by reference, discloses information on PCMCIA conventions and protocols.

Although the embodiment of FIG. 2 is shown comprising a pressure sensor 32 and a disposable spirometry mouthpiece 21, any biological data sensor and/or associated components may be incorporated into the real-time biological data processing PC card 10 in accordance with the present invention.

In one embodiment, each biological data sensor, having a different format of biological data, is configured in a separate real-time biological data processing PC card. The various real-time biological data processing PC cards are interchangeable, to thereby configure the host personal computer 27 into various real-time biological data collecting and processing modes. Alternatively, a single real-time biological data processing PC card 10 may be configured to accommodate one or more different types of biological data sensors. According to the present invention, various interchangeable real-time biological data processing PC cards can configure the host personal computer 27 into various collecting, processing, and monitoring modes, including spirometry, electrocardiography (including resting, 24-hour, stress testing, signal averaging, event ECG, and heart-rate variability), blood pressure, body temperature, electroencephpalography (EEG), echocardioqraphy, Doppler, pulse oximetry (SPO2), sleep analysis, tcPO2, tcPCO2, nitrogen dioxide, capnography, respiratory rate, pulse rate, polysomnography, carbon monoxide, gastroesophageal pH, hydrogen, nitric oxide, bio-impedance, glucometer, audiometry, plethysmograph, weight, electromyography, urometry, and tympanometry, for example. The term "bio-impedance" is intended to include the general meaning of the term "bio-impedance" and to also include body composition analysis, cardiac output or any other bio-impedance analysis. Other biological data may also be collected and processed by the host personal computer 27, after being configured by a corresponding real-time biological data processing PC card.

The real-time biological data processing PC card.10 shown in FIG. 2, which is adapted for configuring the host personal computer 27 for spirometry procedures, receives a pressure signal from the mouth piece 21. The pressure sensor 32, which preferably comprises a pressure transducer, converts the pressure signal into an electrical signal, which is amplified by the amplifier 34. The analog-to-digital converter 36, which is timed by the analog-to-digital timing circuit 38, receives the amplified biological data from the amplifier 34, and digitizes the biological data. The analog-to-digital timing circuit 38 provides a timing signal, which facilitates sampling of the amplified biological data on the conductor path 47. This digitized biological data is output onto the conductor path 50. The storage buffer 41 receives the digitized biological data, and outputs this digitized biological data onto a conductor path 51, where the digitized biological data is made available to the PCMCIA interface 43. The storage buffer 41 preferably comprises a first in first out (FIFO) buffer, and may be omitted for simple configurations where buffering capabilities are not needed. The real-time biological data processing PC card 10 further comprises control circuitry, and the PCMCIA interface 43 preferably comprises input output (I/O) interface glue logic and an input output connector.

Upon insertion of the real-time biological data processing PC card 10 into the PCMCIA format slot 30 of the host computer 27, the microprocessor 61, the PCMCIA interface 70 of the host computer 27, and the PCMCIA interface 43 of the real-time biological data processing PC card 10 begin communicating via established PCMCIA format conventions. The microprocessor 61 determines the type of real-time biological data processing PC card which has been inserted into the PCMCIA format slot 30. In the illustrated case of FIG. 2, designation data from the PCMCIA interface 43 indicates to the microprocessor 61 that a spirometry-type real-time biological data processing PC card 10 has been inserted. Designation data from the PCMCIA interface 43 may, alternatively, identify the real-time biological data processing PC card 10 as being adapted for relaying oximetry, ECG, or other biological data to the host personal computer 27. As an alternative to, or in addition to, the illustrated embodiment of FIG. 2, a user may input designation data via the keyboard 67 or the display 65, indicating the type of real-time biological data processing PC card 10 which has been inserted into the PCMCIA format slot 30 of the host personal computer 27.

After the host personal computer 27 has "set up" the real-time biological data processing PC card 10, the host personal computer 27 prompts, via the display 65, the user to begin the spirometry test. As presently embodied, multimedia devices, such as entertaining displays and sounds, are implemented by the host personal computer 27 in order to educate the patient on how to perform the biological data test. The display 65 prompts the patient to begin the test, and coaches the patient during the test with, for example, entertaining incentives. This multi-media instructional system is configured to assist patients, especially in home disease management situations, helping asthmatics and cystic fibrosis patients, for example, comply with testing protocols. Additionally, the system of the present invention may reduce the need for skilled human interaction in order to achieve successful administration of the biological data tests.

The biological data from the pressure sensor 32, after being processed by the amplifier 34 and the analog-to-digital converter 36, is preferably immediately transferred from the PCMCIA interface 43 of the real-time biological data processing PC card 10 to the PCMCIA interface 70 of the host personal computer 27. The host personal computer 27, having received designation data indicating that the real-time biological data processing PC card 10 is a spirometry real-time biological data processing PC card, is configured to function as a complete spirometry data collecting, processing, and monitoring device. For example, a volume-versus-time wave form or a flow-versus-volume curve may be displayed on the display 65, indicating the real-time biological data received by the pressure sensor 32. A number of other parameters, such as maximum exhale volume, maximum inhale volume, and maximum flow rate, to name a few, may also be shown on the display 65 of the host personal computer 27. This data also may be compiled and printed in a variety of analytical and comparative formats.

Figure 3:
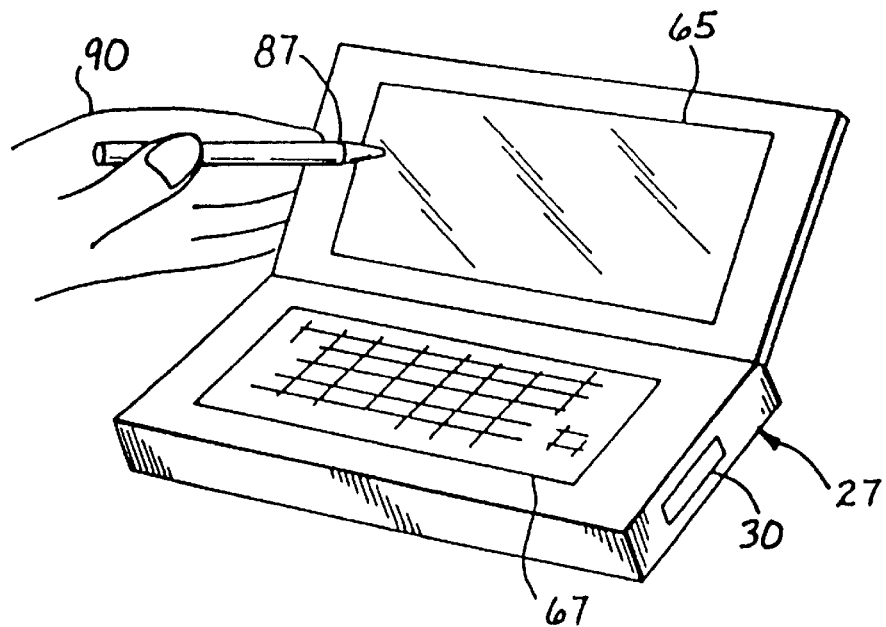
FIG. 3 illustrates a host-personal computer system according to the present invention.

FIG. 3 illustrates a host personal computer 27, according to the presently preferred embodiment. The host personal computer 27 preferably comprises a Personal Digital Assistant (PDA). The host personal computer 27 may comprise any desktop of laptop computer, as well. When the host personal computer 27 comprises a personal digital assistant, as presently preferred, Windows® CE (Pegasus) software is preferably used. This software preferably operates on the Windows® CE operating system. Other commercially available software packages, or customized software packages, may be used with the present invention. A pointing device 87, held by the hand 90 of a user, may be used to input data into the host personal computer 27 via a touch sensitive display 65. The host personal computer 27, having the real-time biological data processing PC card 10 of FIG. 1 inserted therein, is configured into a powerful diagnostic spirometry data collecting and analyzing instrument. Since the real-time biological data processing PC card 10 uses the keyboard 67, display 65, storage 63, microprocessor 61, power supply (not shown), and data transmission and printing capabilities (not shown) of the host computer system 27, the real-time biological data processing PC card 10 itself is very inexpensive and rudimentary in design. Yet, the real-time biological data processing PC card 10 is very powerful. The software loaded within the host personal computer 27 is preferably configured to allow the real-time biological data processing PC card 10 to interface, via PCMCIA format, with any other of a variety of personal computers, such as a desktop personal computer, or a notebook personal computer, for example.

The host personal computer 27 can transmit data via any conventional means, such as a serial port cable or a modem connection through an RJ11 phone plug. Data may be transmitted over the Internet, for example. In home disease management, for example, the host personal computer 27 can be configured to gather, process, and transmit additional information on the patient's medication, diet, symptoms, and other parameters. The combination of elements of the present invention thus provides a very portable, lightweight, and inexpensive means for diagnosing and monitoring patients.

Figure 4:
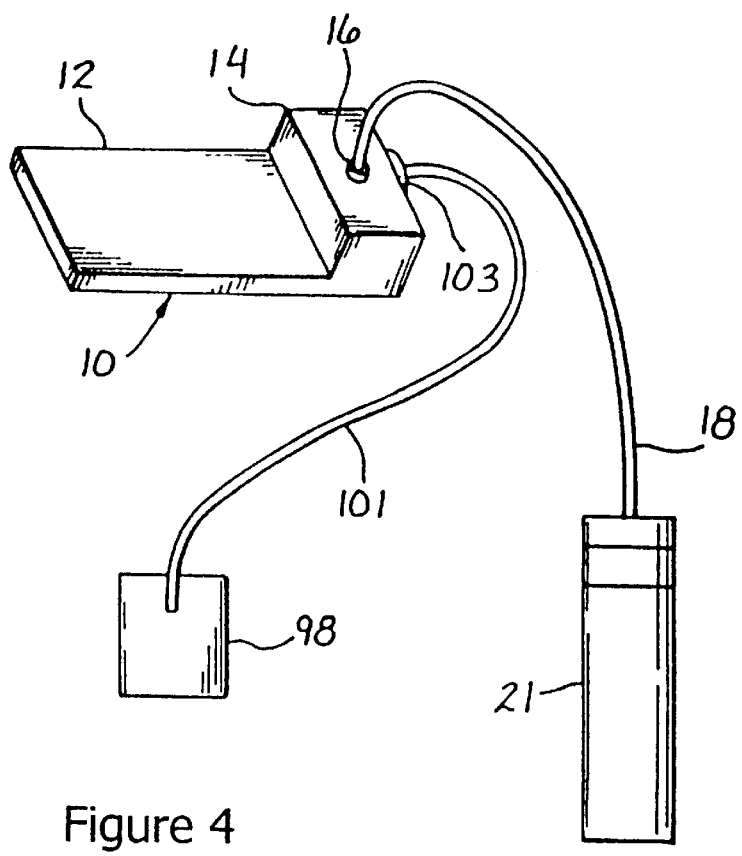
FIG. 4 illustrates a real-time biological data processing PC card according to the present invention.

FIG. 4 illustrates a real-time biological data processing PC card 10, having both a disposable spirometry mouthpiece 21 and a pulse oximeter finger clip 98. Like components are designated with like reference numbers. As with the embodiment of FIG. 1, the disposable spirometry mouthpiece 21 is connected to pressure transducer housing 14 via a flexible air passageway 18 and a pressure input port 16. The pulse oximeter finger clip 98 is connected to the pressure transducer housing 14 via a pulse oximeter cable 101, which transitions into a connector 103.

Figure 5:
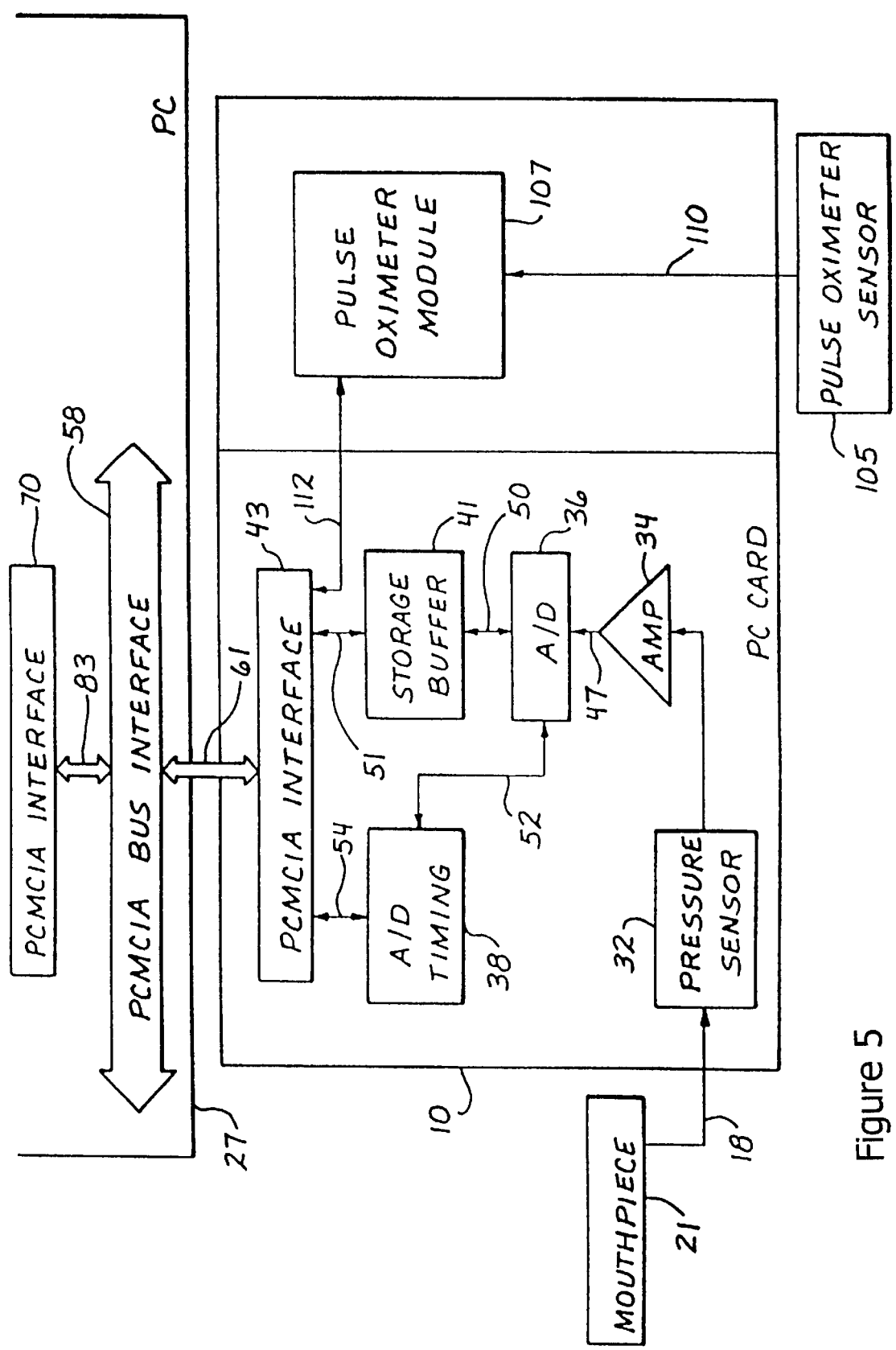
FIG. 5 illustrates a schematic block diagram of the circuitry of the real-time biological data processing PC card according to the present invention.

FIG. 5 illustrates a schematic block diagram of an embodiment of FIG. 4. Basically, data from a pulse oximeter sensor 105, such as the pulse oximeter clip 98 (FIG. 4), is fed to a pulse oximeter module 107 via a conductor path 110. As presently embodied, an optical coupler is positioned between the pulse oximeter finger clip 98 and a power source (not shown) connection of the real-time biological data processing PC card 10, to thereby prevent a patient from being shocked therefrom. Data from the pulse oximeter module 107 is then fed to the PCMCIA interface 43 via a conductor path 112. The pulse oximeter module 107 preferably comprises elements similar to the amplifier 34, the analog-to-digital converter 36, the analog-to-digital timing circuit 38, and the storage buffer 41. The elements of the pulse oximeter module 107 may be combined with or into the elements 34, 36, 38, 41 or, as presently embodied, maintained separately therefrom in the pulse oximeter module 107.

The host personal computer 27 may receive on a real-time basis, process, and monitor spirometry data and pulse oximetry data, either separately or simultaneously. The designation data, in the illustrated embodiment, indicates to the host personal computer 27 that the real-time biological data processing PC card 10 comprises both spirometry data and pulse oximetry data sensors. The pressure sensor 32 may alternatively be located on the disposable spirometry mouthpiece 21, as can the amplifier 34, the analog-to-digital converter 36, and the analog-to-digital timing circuitry 38, or any combination thereof. Any or all of these elements, in addition to the storage buffer 41, may be positioned on either the disposable spirometry mouthpiece 21, the pulse oximeter sensor 105, or the real-time biological data processing PC card 10, or any combination thereof, or eliminated altogether. Since the present invention is not intended to be limited to PCMCIA interfaces 43, any circuitry capable of forwarding an analog signal to a host personal computer 27 could reduce the need for components within the real-time biological data processing PC card 10. The pulse oximeter sensor 105 and the pulse oximeter module 107 may be manufactured by Nonin® Medical, Inc., located in Plymouth, Minn. According to one embodiment, the pulse oximeter sensor 105 may be similiar that in an 8600 portable pulse-oximeter, manufactured by Nonin® Medical, Inc.

FIG. 6a illustrates the main circuit board 118 of the presently preferred embodiment, generally corresponding to the elements 32–54 of FIG. 5. The main circuit board 118 is illustrated comprising a number of IC chips 121, a pressure input port 16, and a pressure sensor 32. A pulse oximetry module connector 125 accommodates a pulse oximetry module connector 127, which is illustrated in FIG. 6b. The pulse oximetry module connector 127 of FIG. 6b is electrically connected to a supplemental circuit board 130. The supplemental circuit board 130 generally corresponds to the pulse oximeter module 107 of FIG. 5.

FIG. 7 illustrates a perspective view of a pulse oximeter finger clip 98 connected to a hand 87 of a user. The pulse oximeter finger clip 98 is connected to the supplemental circuit board 130 via a pulse oximeter cable 101.

Figure 8:
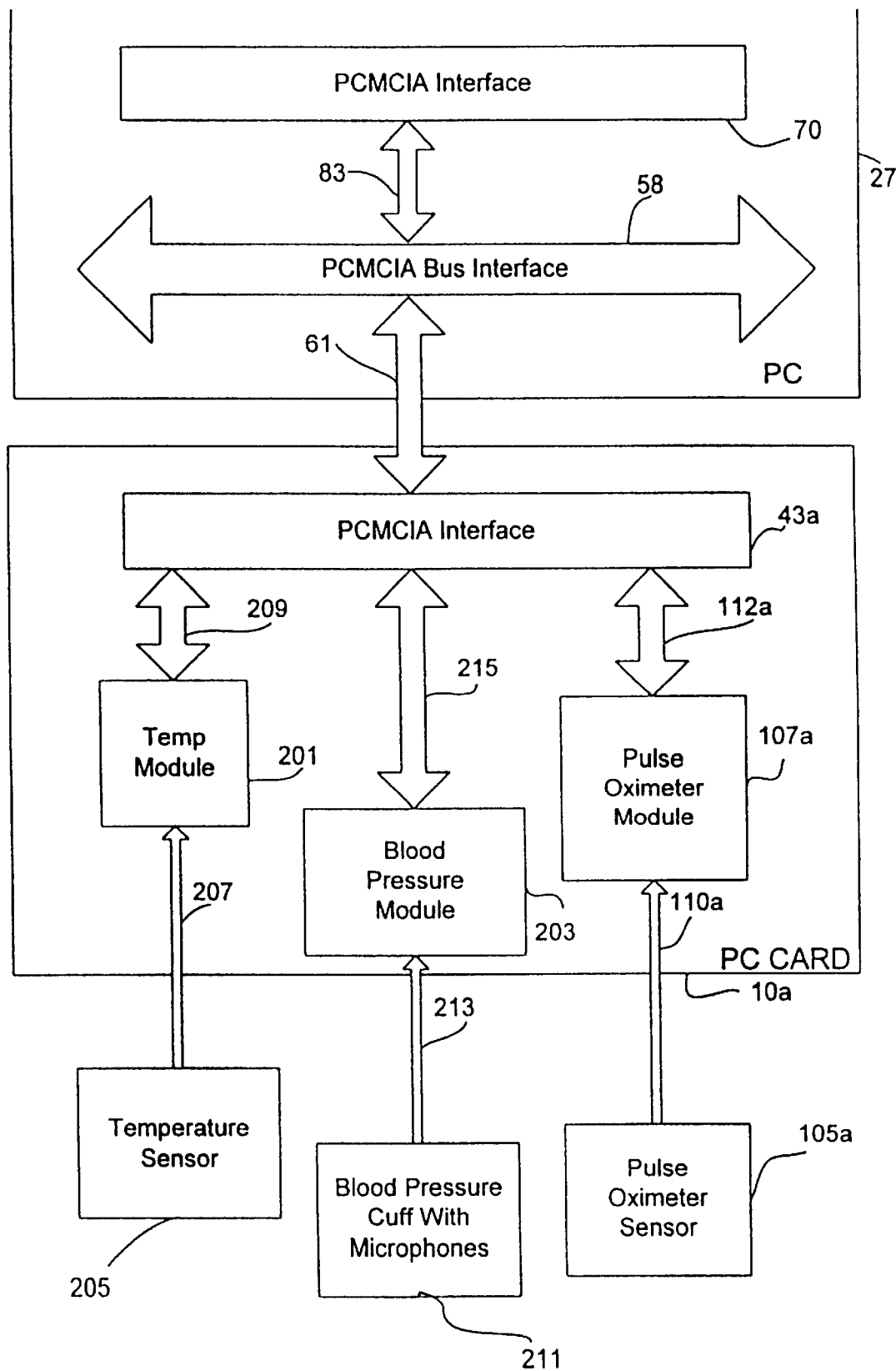
FIG. 8 illustrates a schematic block diagram of a real-time biological data processing PC card for collecting and forwarding on a real-time basis vitals data.

FIG. 8 illustrates a schematic block diagram of a real-time biological data processing PC card 10a for collecting and forwarding on a real-time basis vitals data. In the embodiment of FIG. 8, like elements are designated with like reference numerals followed by the letter "a." Data from a pulse oximeter sensor 105a is fed to a pulse oximeter module 107a via a conductor path 110a. As presently embodied, an optical coupler is positioned between a pulse oximeter finger clip (not shown) and a power source (not shown) connection of the real-time biological data processing PC card 10a, to thereby prevent a patient from being shocked therefrom. Data from the pulse oximeter module 107a is then fed to the PCMCIA interface 43a via a conductor path 112a. The pulse oximeter module 107a may comprise conventional circuitry for processing data from the pulse oximeter sensor 105a, such as elements including an amplifier, an analog-to-digital converter, an analog-to-digital timing circuit, and a storage buffer. The elements of the pulse oximeter module 107a may be combined with or into the elements of the temperature module 201 and the blood pressure module 203 or, as presently embodied, maintained separately therefrom in the pulse-oximeter module 107a.

Data from a temperature sensor 205, indicating a body temperature of a patient, is fed to the temperature module 201 via a conductor path 207. Data from the temperature module 201 is then fed to the PCMCIA interface 43a via a conductor path 209. The temperature module 201 may comprise conventional circuitry for processing data from the temperature sensor 205, such as elements including an amplifier, an analog-to-digital converter, an analog-to-digital timing circuit, and a storage buffer. The elements of the temperature module 201 may be combined with or into the elements of the pulse oximeter module 107a and/or the elements of the blood pressure module 203 or, as presently embodied, maintained separately therefrom in the temperature module 201.

Data from a blood pressure sensor 211, indicating a blood pressure of a patient, is fed to the blood pressure module 203 via a conductor path 213. Data from the blood pressure module 203 is then fed to the PCMCIA interface 43a via a conductor path 215. The blood pressure sensor 211 preferably comprises a cuff with microphones as is known in the art. The blood pressure module 203 may comprise conventional circuitry for processing data from the blood pressure sensor 211, such as elements including an amplifier, an analog-to-digital converter, an analog-to-digital timing circuit, and a storage buffer. The elements of the blood pressure module 203 may be combined with or into the elements of the pulse oximeter module 107a and/or the elements of the temperature module 201 or, as presently embodied, maintained separately therefrom in the blood pressure module 203.

As presently embodied, a host personal computer 27 receives on a real-time basis, processes, and monitors pulse oximetry data, body temperature data, and blood pressure data either separately, sequentially, or simultaneously. The designation data, in the presently preferred embodiment, indicates to the host personal computer 27 that the real-time biological data processing PC card 10a comprises pulse oximetry data, temperature data and blood pressure data sensors. One or more of the components comprising the pulse oximeter module 107a, the temperature module 201 and/or the blood pressure module 203 may alternatively be located on the respective sensors 105a, 205, 211.

Figure 9:
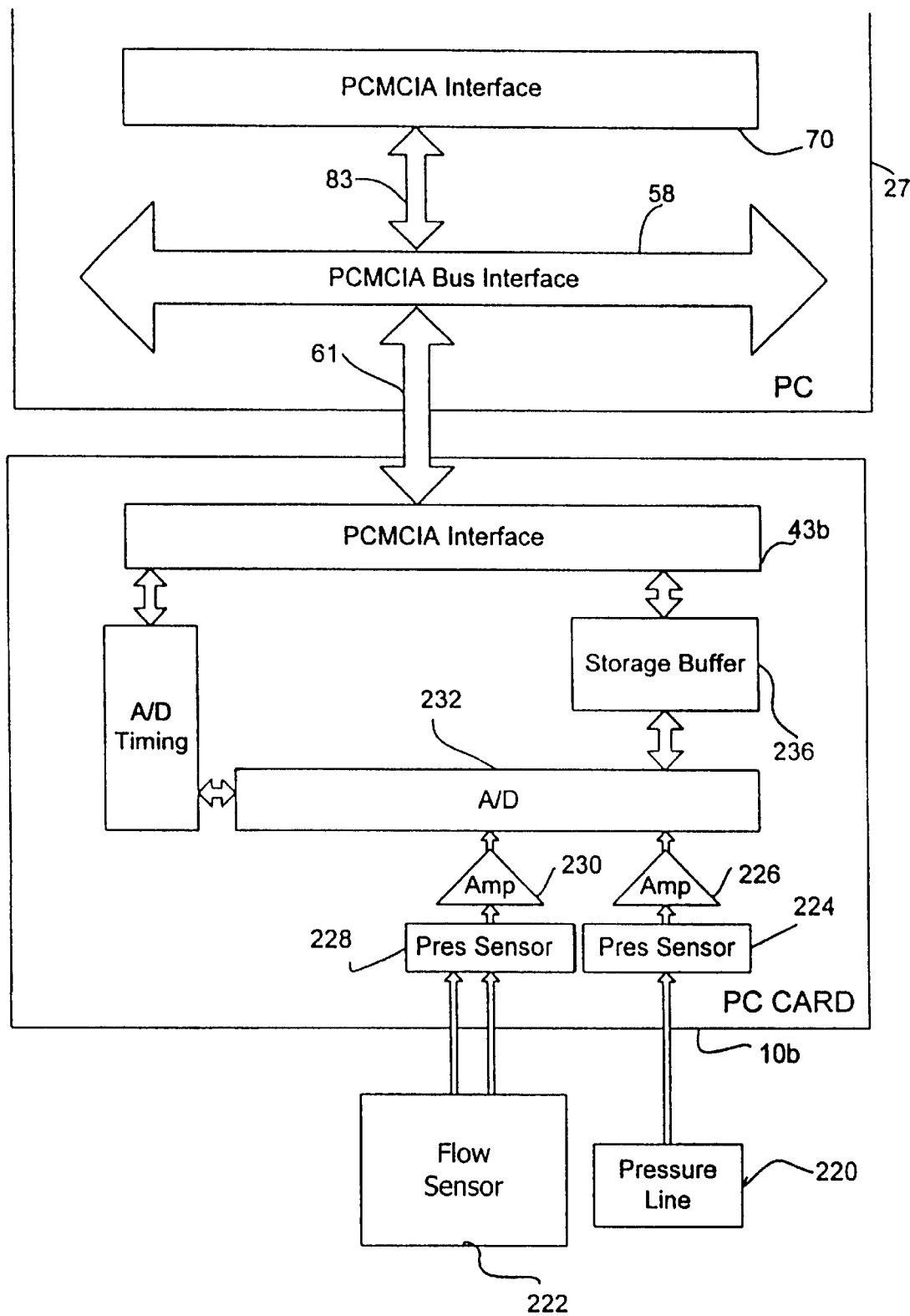
FIG. 9 illustrates a schematic block diagram of a real-time biological data processing PC card for collecting and forwarding on a real-time basis ventilator-operation data.

Turning to FIG. 9, a schematic block diagram of a real-time biological data processing PC card for collecting and forwarding on a real-time basis ventilator operation data is shown. In the embodiment of FIG. 9, like elements are designated with like reference numerals followed by the letter "b." A pressure line 220 and flow line 222 are connected to monitor pressure and flow rate of a ventilator connected to a patient. The pressure line inputs pressure data from a hose of the ventilator to a pressure sensor 224 and, subsequently, to an amplifier 226. The flow line 222 are input into the pressure sensors 228 and the amplifier 230. An analog-to-digital converter 232 receives the signals from the amplifiers 226 and 230, and converts the signals to digital signals. The digital signals are forwarded to the PCMCIA interface 43b via a storage buffer 236.

The host personal computer 27 receives on a real-time basis, processes and monitors the pressure and flow rate data from the sensors 220 and 222 either separately, sequentially or simultaneously. The designation data indicates to the host personal computer 27 that the real-time biological data processing PC card 10b comprises pressure and flow rate data from a ventilator hose connected to a patient. One or more of the components of the PC card may be placed on the pressure line 220 or the differential flow line 222.

Figure 10:
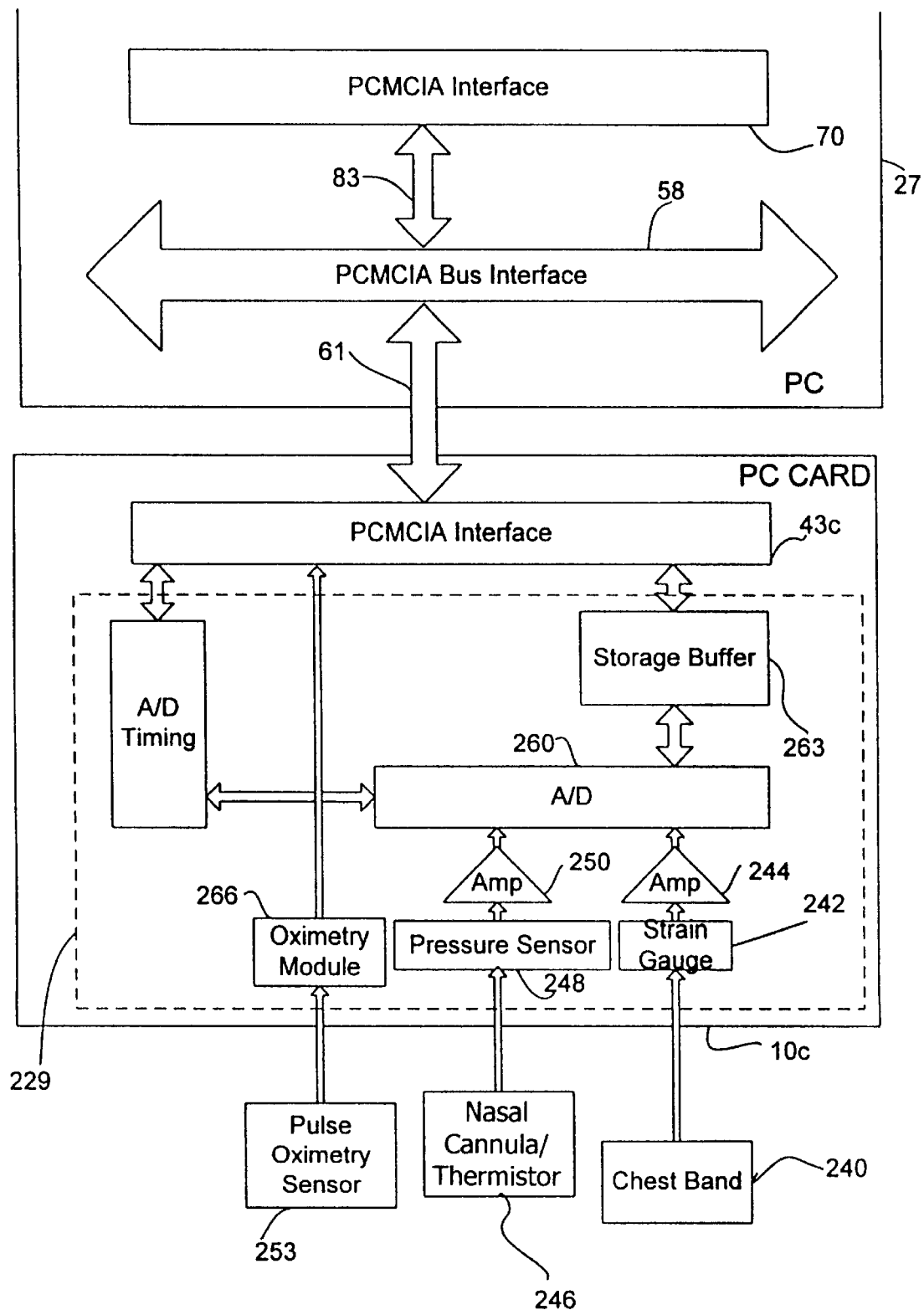
FIG. 10 illustrates a schematic block diagram of a real-time biological data processing PC card for collecting and forwarding on a real-time basis sleep-disorder related data.

FIG. 10 illustrates a schematic block diagram of a real-time biological data processing PC card for collecting and forwarding on a real-time basis, sleep-disorder related data. A chest band 240 is placed around a patient's chest to measure the patient's respiration rate, for example. Sensors on the chest band 240 measure movement of the patient's chest while the patient is sleeping for determining, for example, whether the patient is breathing through his or her nose and whether an obstruction is present. Data from sensors on the chest band 240 is input into a strain gauge 242 and subsequently amplified by an amplifier 244. A nasal canula/thermistor 246 measures breathing through a patient's nose, and the data therefrom is input into a pressure sensor 248 and subsequently amplified by the amplifier 250. A pulse oximetry sensor 253 measures the patient's pulse rate and/or blood-oxygen concentration. Data from the chest band 240 and the nasal canula/thermistor 246 is digitized by the analog-to-digital converter 260 and passed to the PCMCIA interface 43c via a storage buffer 263. Data from the pulse oximetry sensor 253 is similarly passed to the PCMCIA interface 43c after being processed by an oximetry module 266. The data from the chest band 240, the nasal canula/thermistor 246 and the pulse oximetry sensor 253 is transferred to the host personal computer 27 on a real-time basis, either separately, sequentially of simultaneously.

Figure 11:
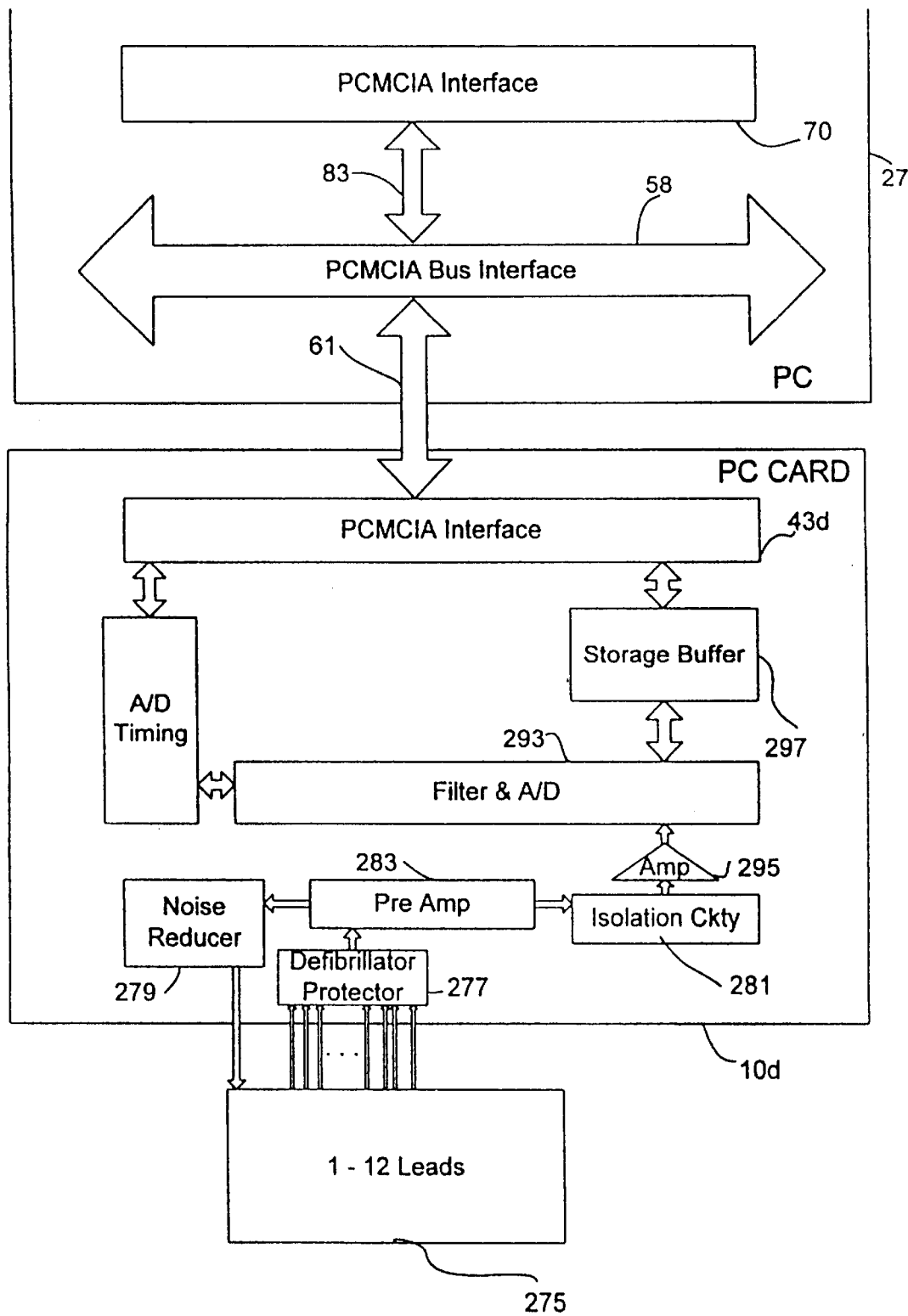
FIG. 11 illustrates a schematic block diagram of a real-time biological data processing PC card for collecting and forwarding on a real-time basis ECG data.

FIG. 11 illustrates a schematic block diagram of a real-time biological data processing PC card for collecting and forwarding on a real-time basis ECG data. One to twelve leads 275 are attached to a patient for inputting ECG data to a defibrillator protector 277. The defibrillator protector 277 accommodates operation of the PC card 10d when the patient is defibrillated, as is known in the art. Conventional noise reduction 279 and isolation 281 components receive data from the preamp 283. Data from the isolation circuitry 281 is input to a filter and analog-to-digital conversion module 293 via an amplifier 295. The ECG data is input into a PCMCIA interface 43d via a storage buffer 297. The noise reducer 279 may comprise, for example, a driven right leg and driven shield configuration, wherein an ECG signal from the leads 275 is inverted and injected back into the patient's right leg to cancel noise. The driven shield comprises a similar mechanism for reducing noise as is known in the art.

The PC card 10d may be configured to implement a signal averaging mode of ECG data collection, wherein a relatively high sampling rate of 2,000 to 3,000 samples per second is implemented, for example. The samples are subsequently averaged for providing additional resolution, compared to a slower sampling rate such as 250 samples per second. Moreover, instead of implementing one to twelve leads for feeding electrical signals from the patient to the PC card 10d, a wireless embodiment may be implemented. In this embodiment, electrical signals from the patient are transmitted to a receiver on a PC card, for example. Processed data from the twelve leads 275 is transferred from the PC card 10d to the host personal computer 27 on a teal-time basis in accordance with the present invention.

Figure 12:
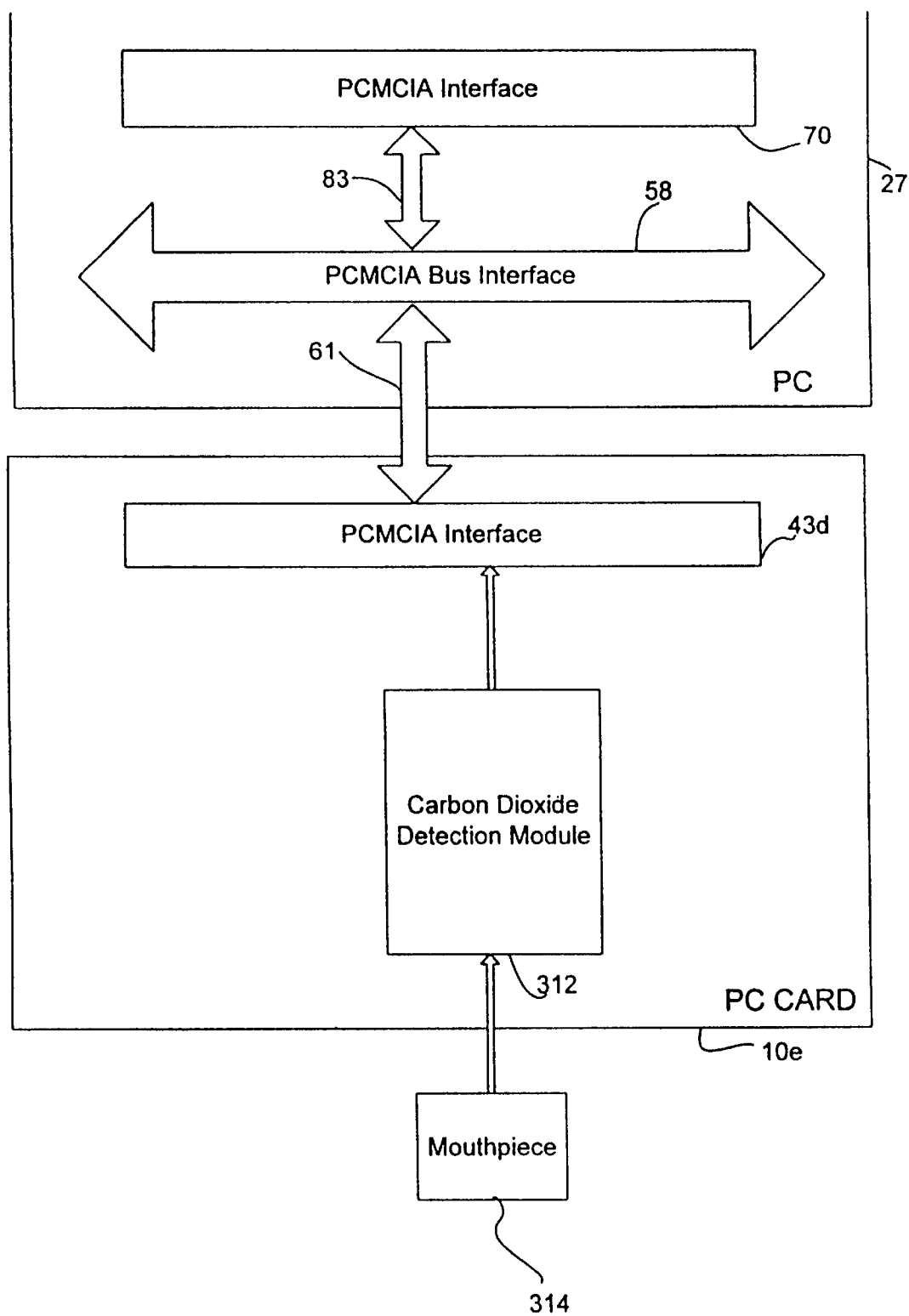
FIG. 12 illustrates a schematic block diagram of a real-time biological data processing PC card for collecting and forwarding on a real-time basis carbon-dioxide detection data.
Figure 13:
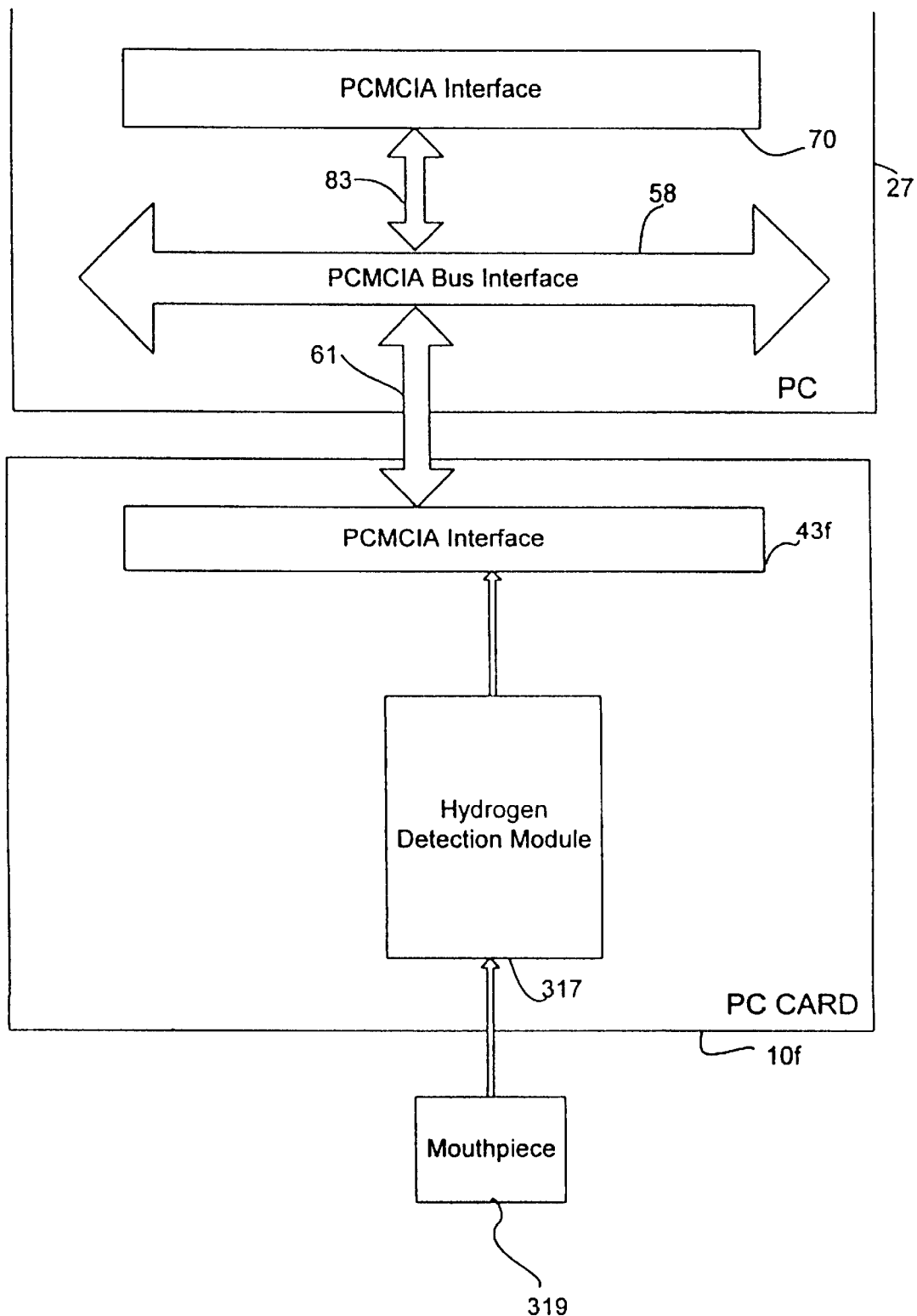
FIG. 13 illustrates a schematic block diagram of a real-time biological data processing PC card for collecting and forwarding on a real-time basis hydrogen detection data.
Figure 14:
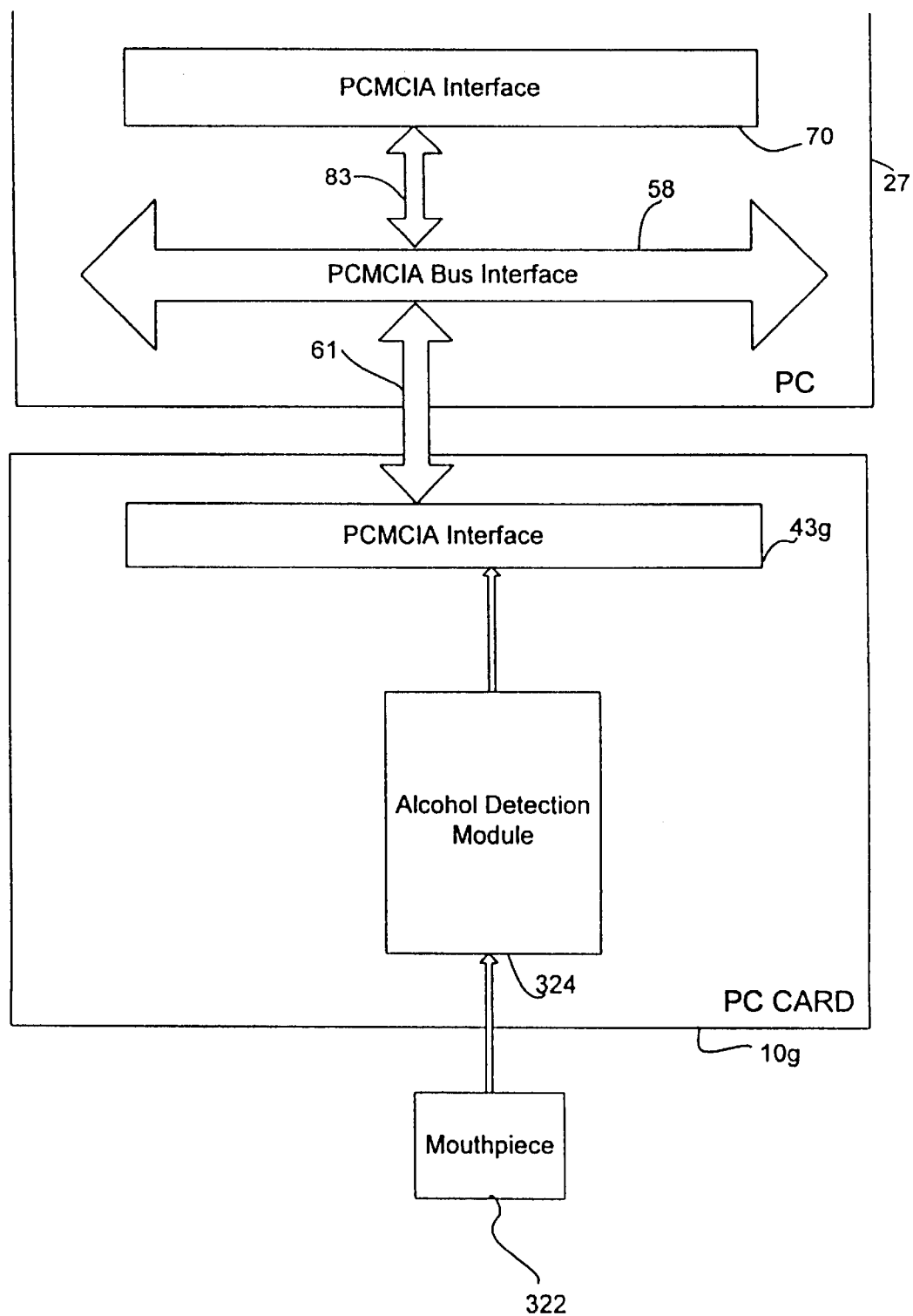
FIG. 14 illustrates a schematic block diagram of a real-time biological data processing PC card for collecting and forwarding on a real-time basis alcohol detection data.

Turning to FIG. 12, a PC card 10e for collecting and forwarding on a real-time basis carbon dioxide detection data to a host personal computer 27 on a real-time basis is disclosed. Carbon dioxide in the breath of a patient is detected by a carbon dioxide detection module 312, after being input through a mouthpiece 314. FIG. 13 illustrates a-hydrogen detection module 317 within a PC card 10f. A patient breathes into a mouthpiece 319. A reading on a detected amount of hydrogen is forwarded to the PC card 27 via a PCMCIA interface 43f of the PC card 10f on a real-time basis. As shown in FIG. 14, a real-time biological data processing PC card 10g collects breath from a user via a mouthpiece 322. An amount of alcohol in the user's breath is detected by an alcohol detection module 324, which sends digital data to the PCMCIA interface 43g for subsequent routing on a real-time basis to the personal computer 27.

Figure 15:
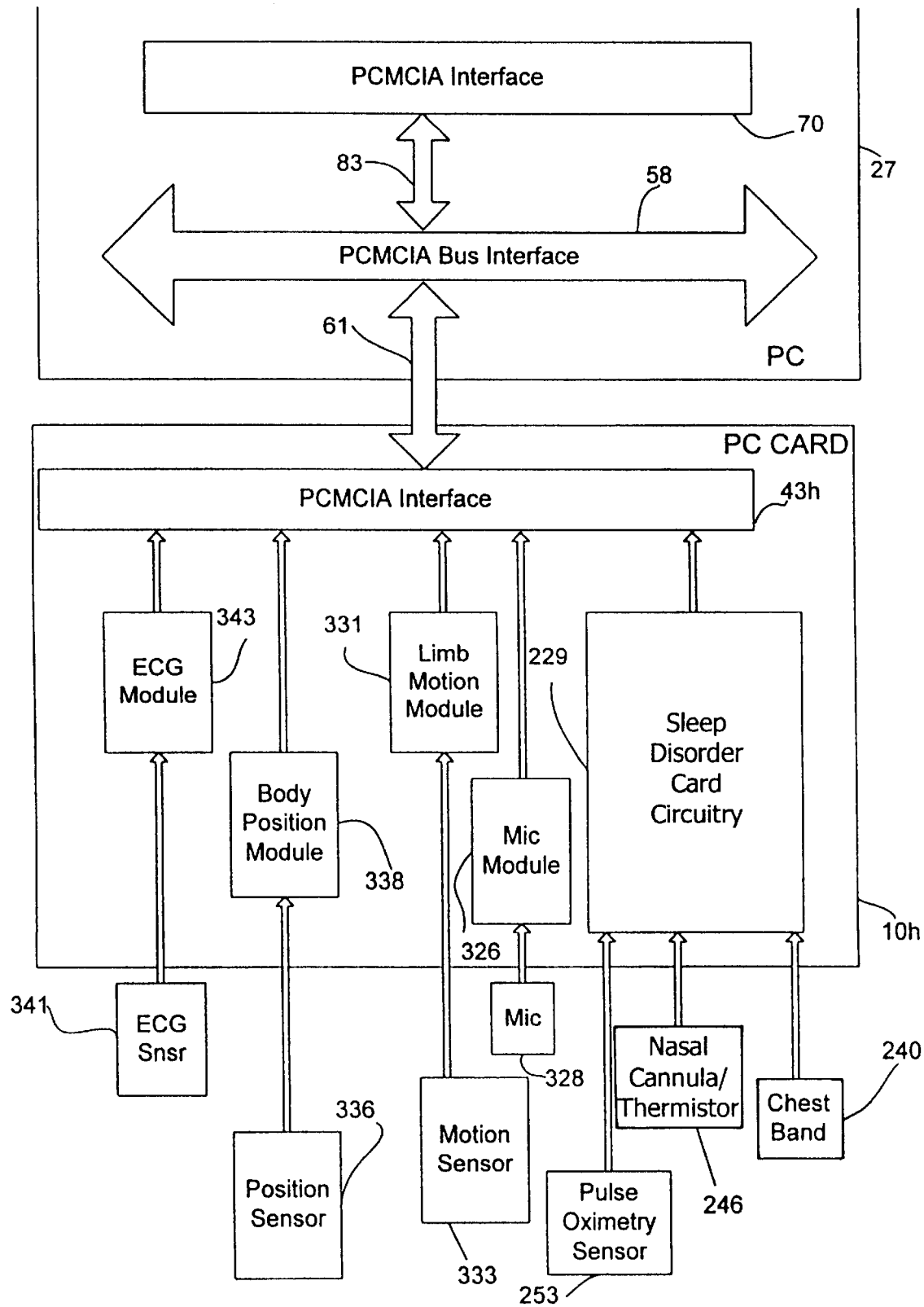
FIG. 15 illustrates a schematic block diagram of a real-time biological data processing PC card for collecting and forwarding on a real-time basis sleep-disorder related data including body motion and position and ECG.

A real-time biological data processing PC card for collecting and forwarding on a real-time basis sleep-disorder related data including body motion and position, and ECG, is shown in FIG. 15. The apnea card circuitry generally corresponds to that disclosed in FIG. 10, and the PC card 10h further comprises a microphone module 326 for receiving sound signals from a microphone 328 and forwarding digitized signals on a real-time basis to the PCMCIA interface 43h. A limb motion module 331 inputs data from motion sensors 333. Data from the motion sensor or sensors 333 is processed by the limb motion module 331 and forwarded on a real-time basis to the PCMCIA interface 43h. Position data from a position sensor 336 is forwarded to the body position module 338, processed, and subsequently forwarded on a real-time basis to the PCMCIA interface 43h. The microphone 328 can be attached to a neck of a patient, for example, for providing information as to whether the patient is snoring. The motion sensor 333 may comprise an accelerometer, for example, and may be attached to a limb of a patient to determine limb and/or body motion. The position sensor 336 may comprise a mercury switch, for example, and may be attached to a portion of a patient to determine whether the patient is lying on his or her stomach or back, for example. An ECG sensor 341 may comprise one or two channels, for example, for inputting electrical information to the ECG module 343. Processed information from the ECG module 343 is subsequently forwarded on a real-time basis to the PCMCIA interface 43h.

Figure 16:
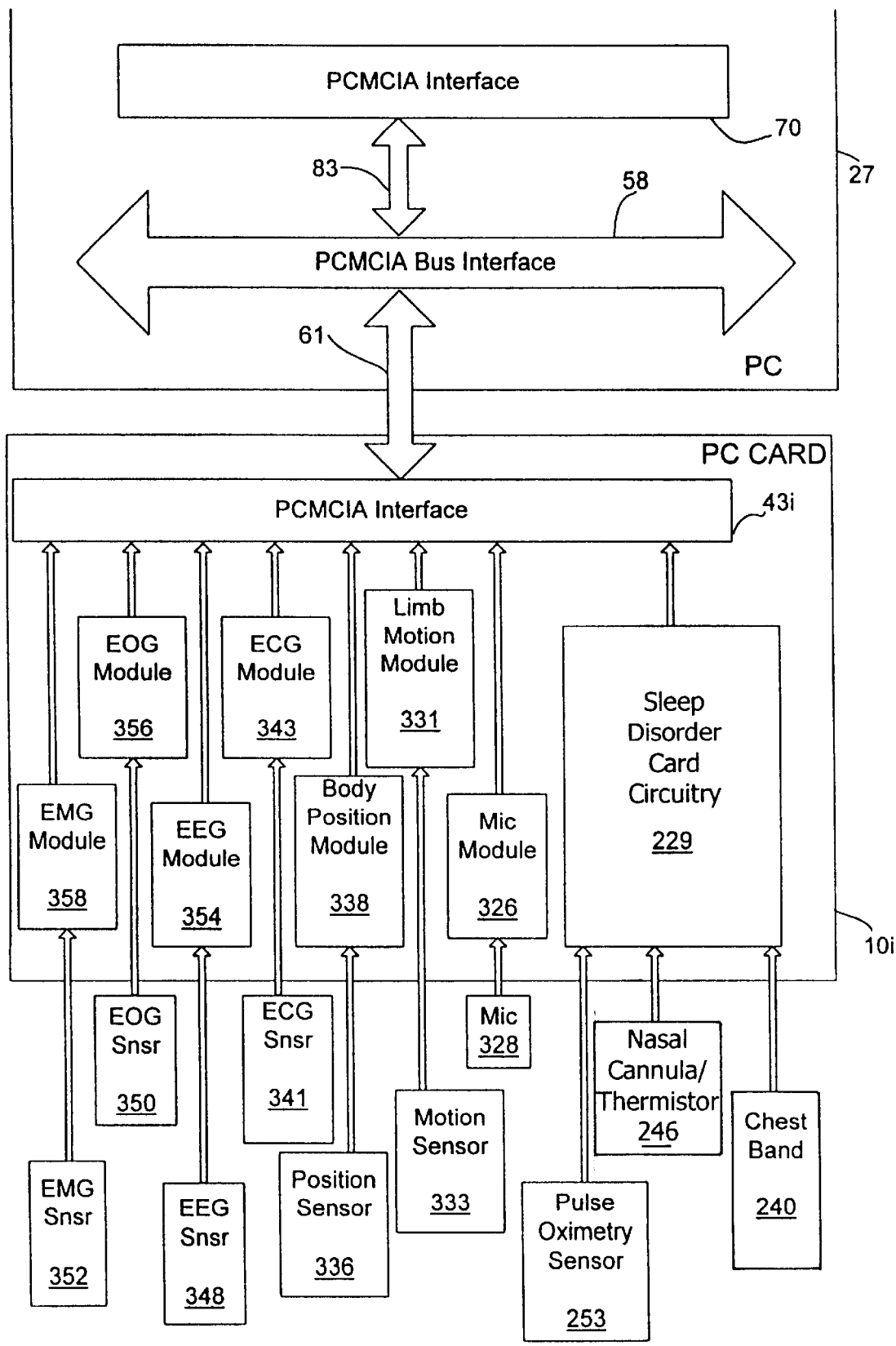
FIG. 16 illustrates a schematic block diagram of a real-time biological data processing PC card for collecting and forwarding on a real-time basis sleep-disorder related data including body motion and position, ECG, EOG and EMG.

The PC card 10i of FIG. 16 is similar to that depicted in FIG. 15, with additional EEG, EOG, and EMG components. An EEG sensor 348, an EOG sensor 350 and an EMG sensor 352 forward signals detected on a patient to an EEG module 354, an EOG module 356, and an EMG module 358, respectively, on a real-time basis. The EEG module 354, the EOG module 356 and the EMG module 358 forward processed data to the PCMCIA interface 43i on a real-time basis and, subsequently, as with the other embodiments of the present invention, the PCMCIA interface 43i preferably forwards the real-time data to the host personal computer 27 on a real-time basis.

Figure 17:
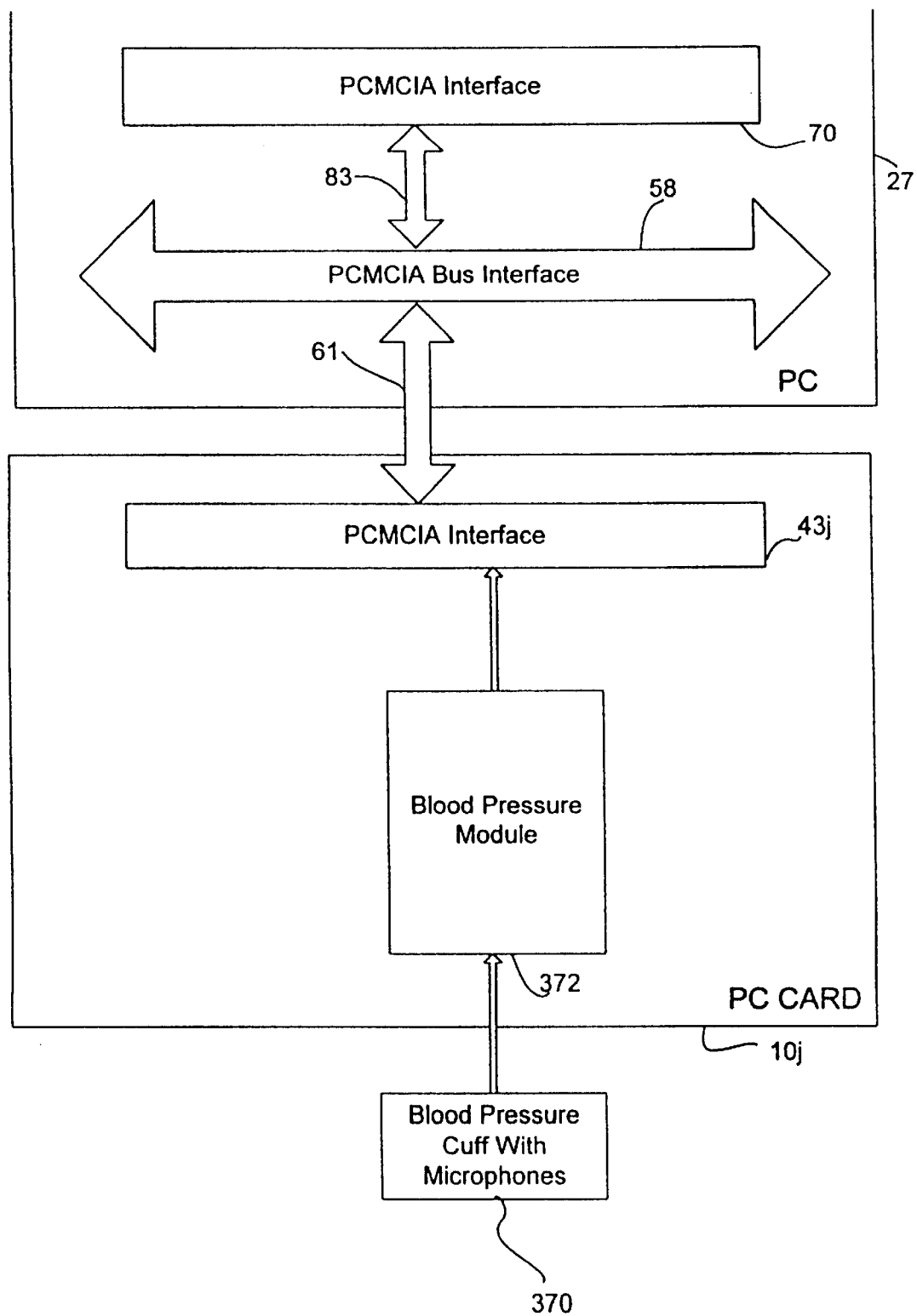
FIG. 17 illustrates a schematic block diagram of a real-time biological data processing PC card for collecting and forwarding on a real-time basis blood pressure related data.

Turning to FIG. 17, a real-time biological data processing PC card 10j inputs blood pressure data from a blood pressure sensor 370 on a real-time basis. The blood pressure sensor preferably comprises a blood pressure cuff with microphones. A blood pressure module 372 receives the data from the sensor 370 and forwards processed digitized data on a real-time basis to the PCMCIA interface 43j.

Figure 18:
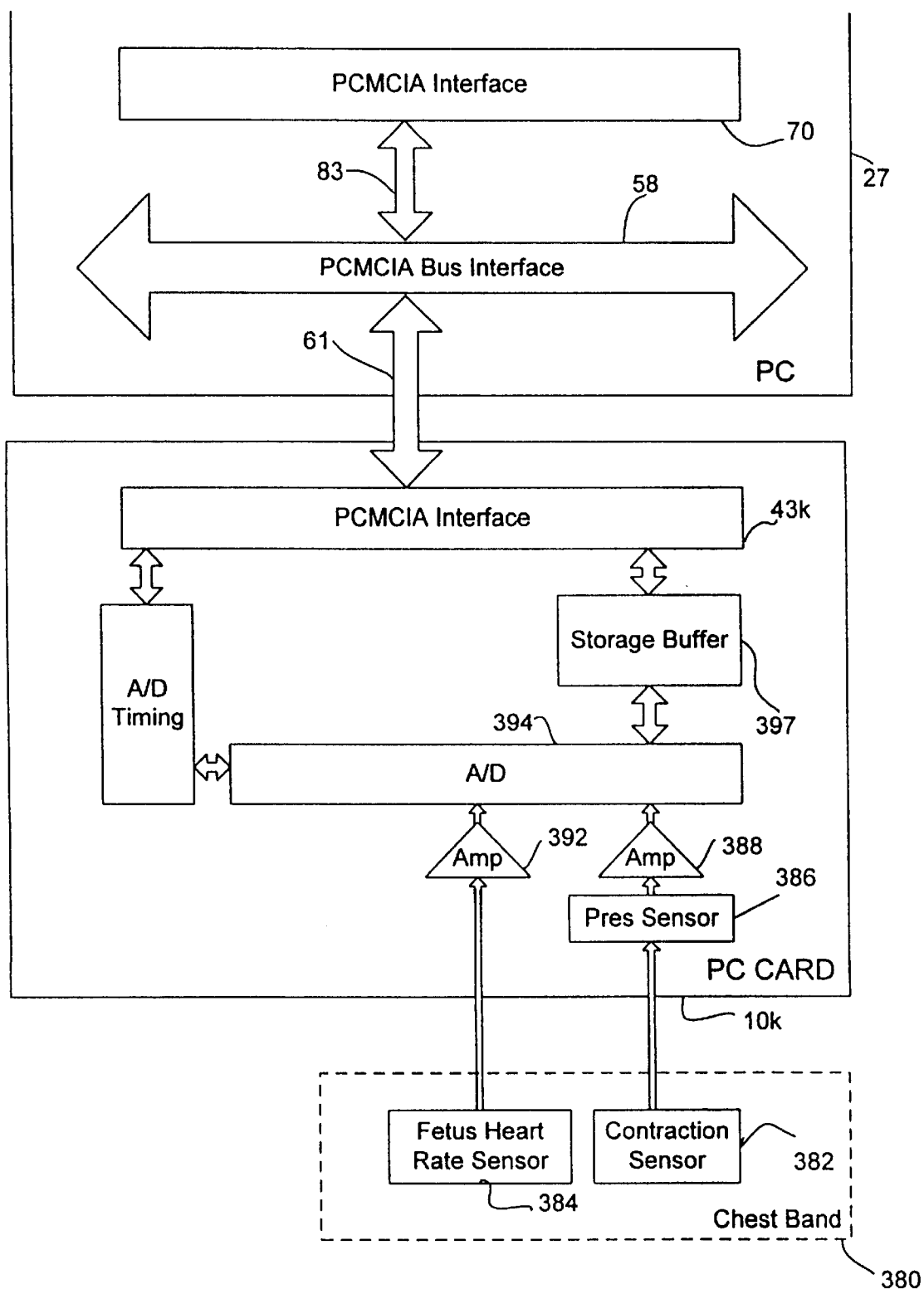
FIG. 18 illustrates a schematic block diagram of a real-time biological data processing PC card for collecting and forwarding on a real-time basis birth procedure related data.

FIG. 18 illustrates a real-time biological data processing PC card for collecting and forwarding on a real-time basis birth procedure related data. A chest band 380 comprises a contraction sensor 382 and a fetus heart rate sensor 384. The contraction sensor 382 may comprises a pressure sensor, for example, which is adapted to be disposed on a woman's stomach via the chest band 380, and the fetus heart rate sensor 384 may comprise a microphone. An additional sensor (not shown) may also be incorporated for monitoring on a real-time basis the mother's heart rate. The additional sensor may comprise, for example, a pulse oximeter. Data from the contraction sensor 382 and the fetus heart rate sensor 384 is input into the pressure sensors and amplifiers 386, 388, 390, 392. An analog-to-digital converter 394 processes the information and outputs the information to the PCMCIA interface 43k via a storage buffer 397.

Figure 19:
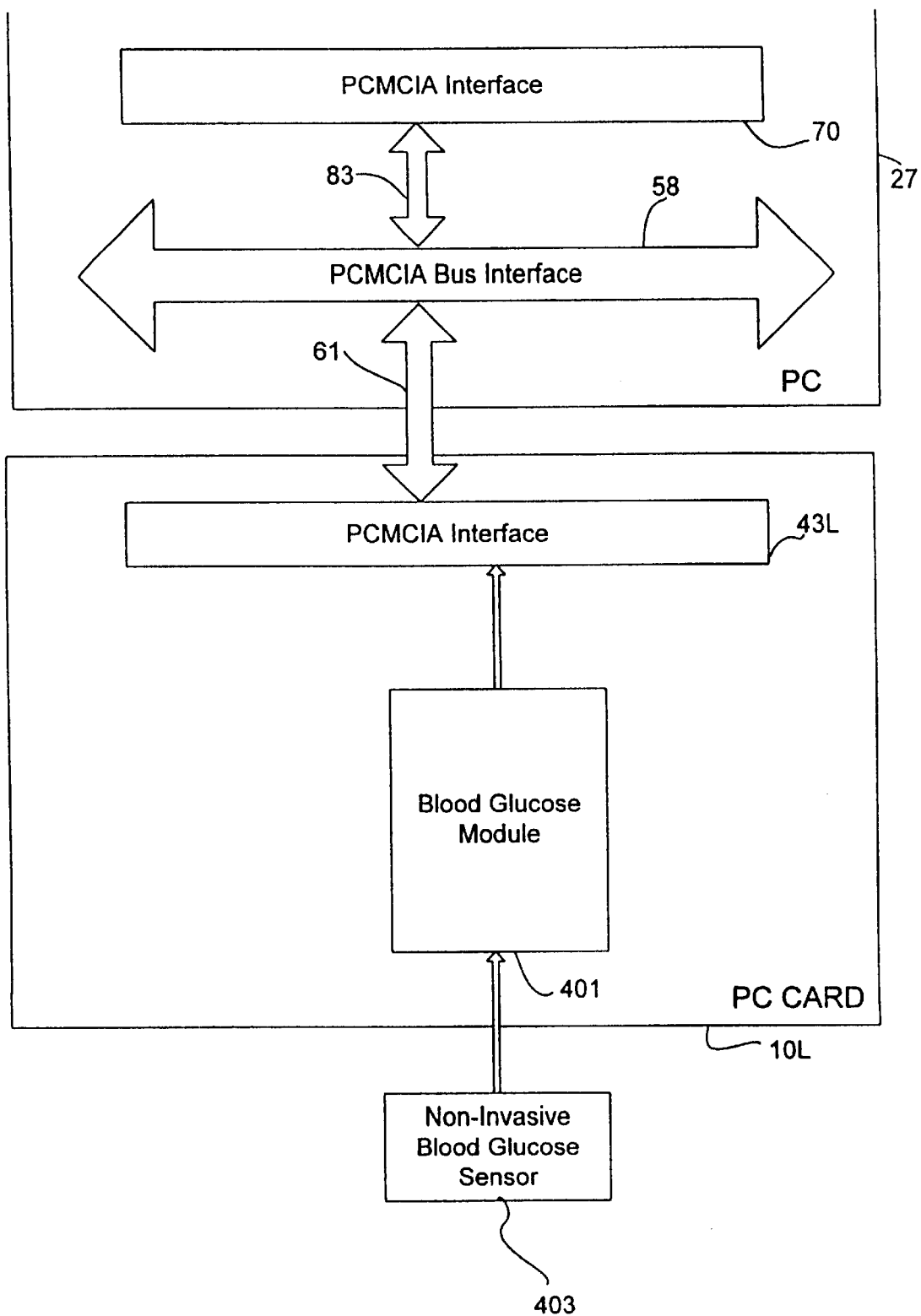
FIG. 19 illustrates a schematic block diagram of a real-time biological data processing PC card for collecting and forwarding on a real-time basis blood glucose detection data.
Figure 20:
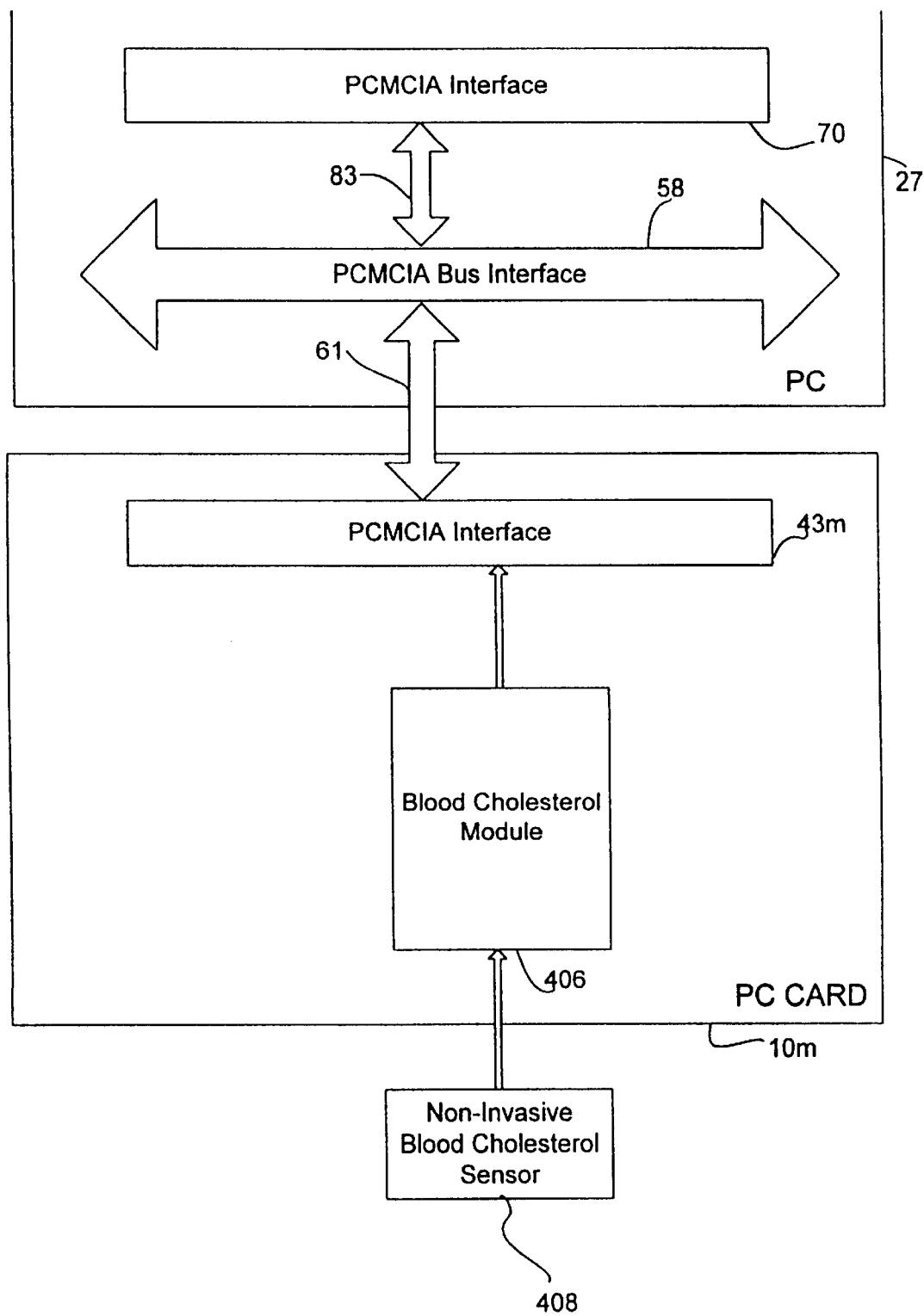
FIG. 20 illustrates a schematic block diagram of a real-time biological data processing PC card for collecting and forwarding on a real-time basis blood cholesterol detection data.
Figure 21:
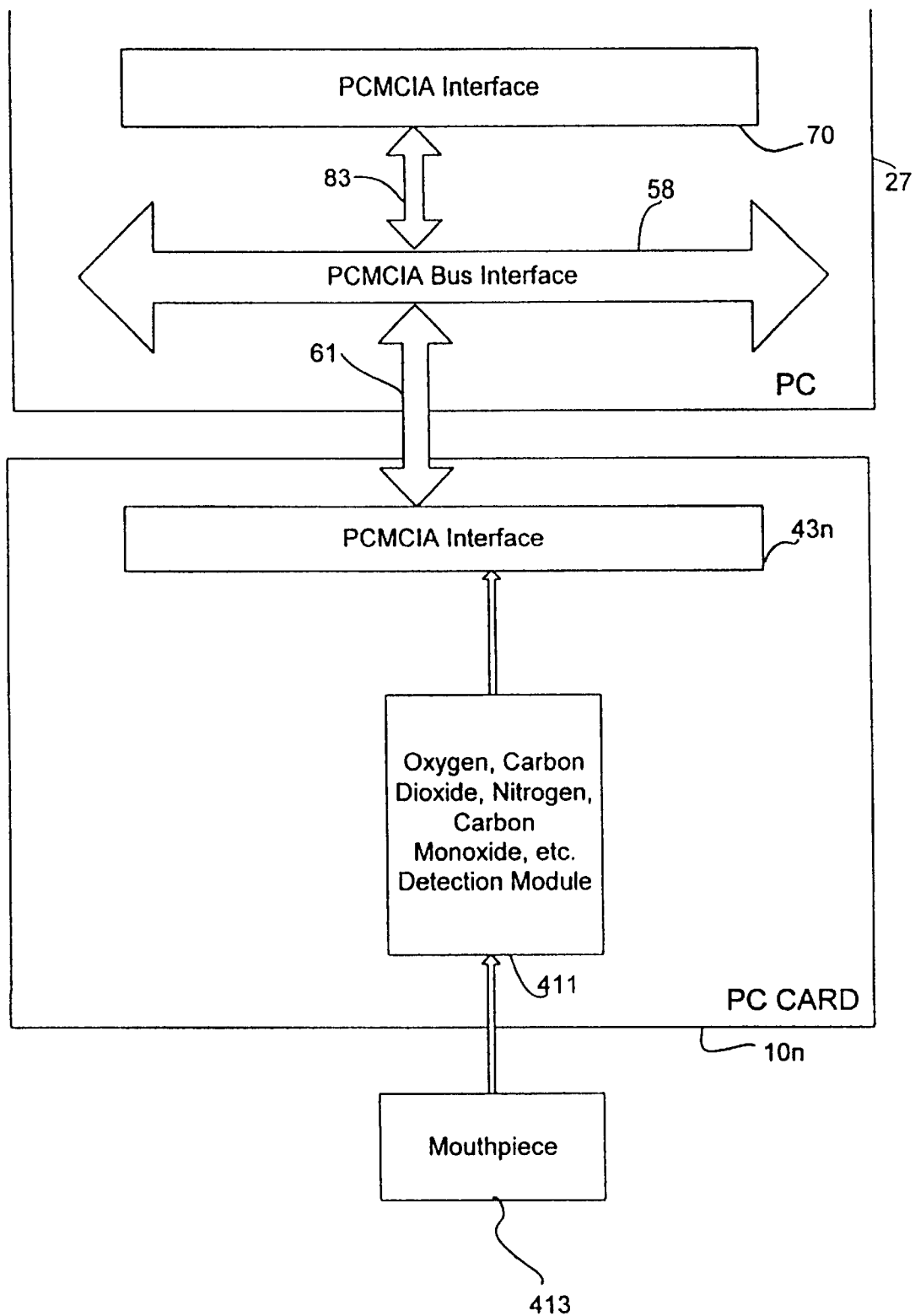
FIG. 21 illustrates a schematic block diagram of a real-time biological data processing PC card for collecting and forwarding on a real-time basis blood arterial-blood-gas detection data.
Figure 22:
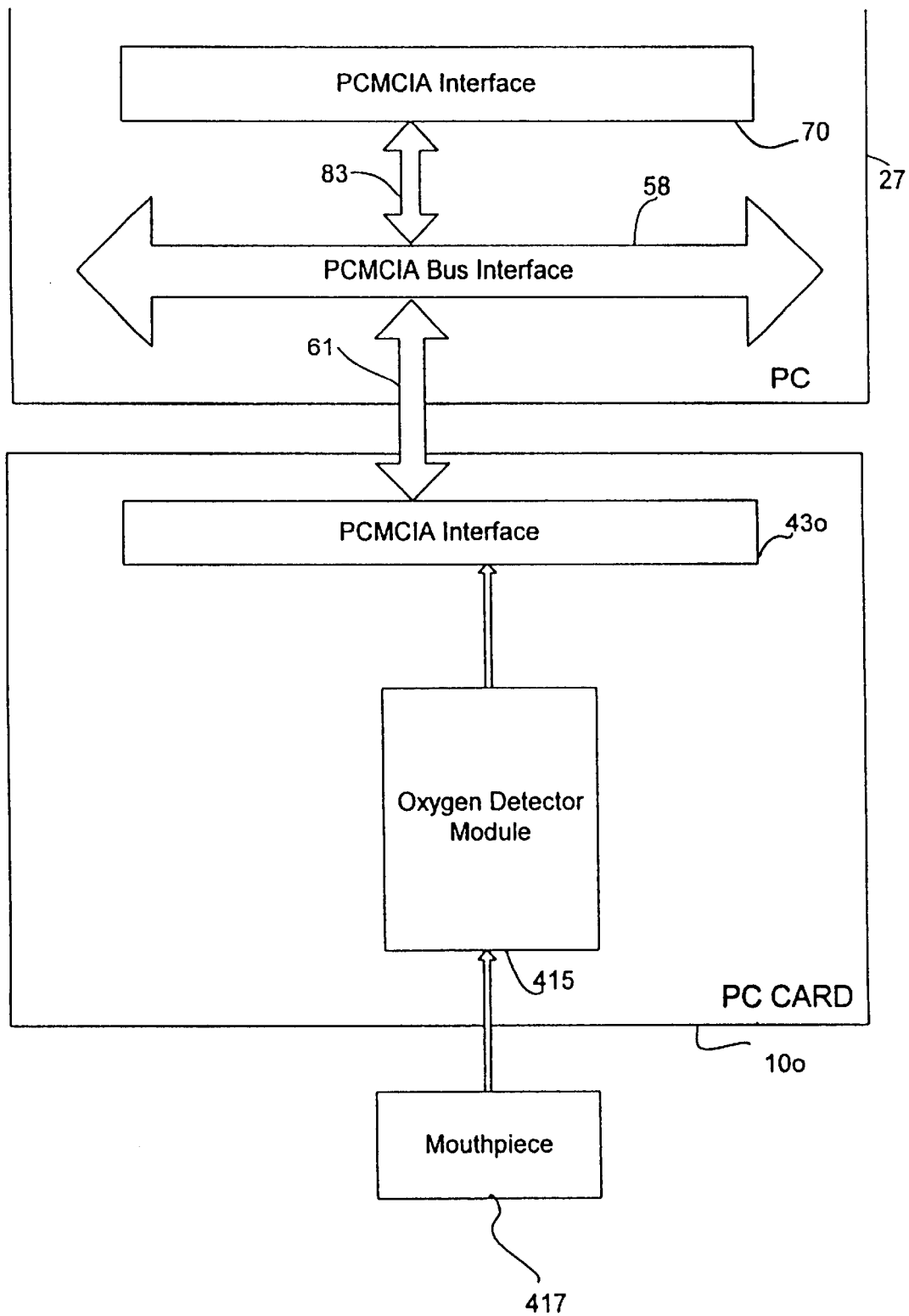
FIG. 22 illustrates a schematic block diagram of a real-time biological data processing PC card for collecting and forwarding on a real-time basis oxygen detection data.

FIGS. 19, 20, and 21 illustrate non-invasive blood composition detection PC cards 10L, 10m and 10n, respectively, for collecting on a real-time basis biological data and forwarding the data on a real-time basis to a host personal computer 27. The blood glucose module 401 of the PC card 10L inputs blood glucose data from a non-invasive blood glucose sensor 403 on a real-time basis. The non-invasive blood glucose sensor 403 may comprise any conventional means for measuring a blood glucose concentration of a patient, such as, for example, a patch adapted to be attached to a person's skin or an optical measuring apparatus. A blood cholesterol module 406 of the PC card 10m (FIG. 20) inputs blood cholesterol data from a non-invasive blood cholesterol sensor 408. The non-invasive blood cholesterol sensor 408 may comprise any non-invasive blood-cholesterol measuring apparatus. The detection module 411 (FIG. 21) of the PC card 10n is adapted to receive a breath of a patient via a mouthpiece 413, and detect on a real-time basis gases including, oxygen, carbon dioxide, nitrogen and/or carbon monoxide. Each of the modules 401, 406 and 411 forwards processed sensor data on a real-time basis to the PCMCIA interfaces 43L, 43m and 43n, respectively. FIG. 22 illustrates a PC card 10o comprising an oxygen detector 415 for inputting breath from a mouthpiece 417 and forwarding processed data on a real-time basis to a PCMCIA interface 43*o*.

Figure 23:
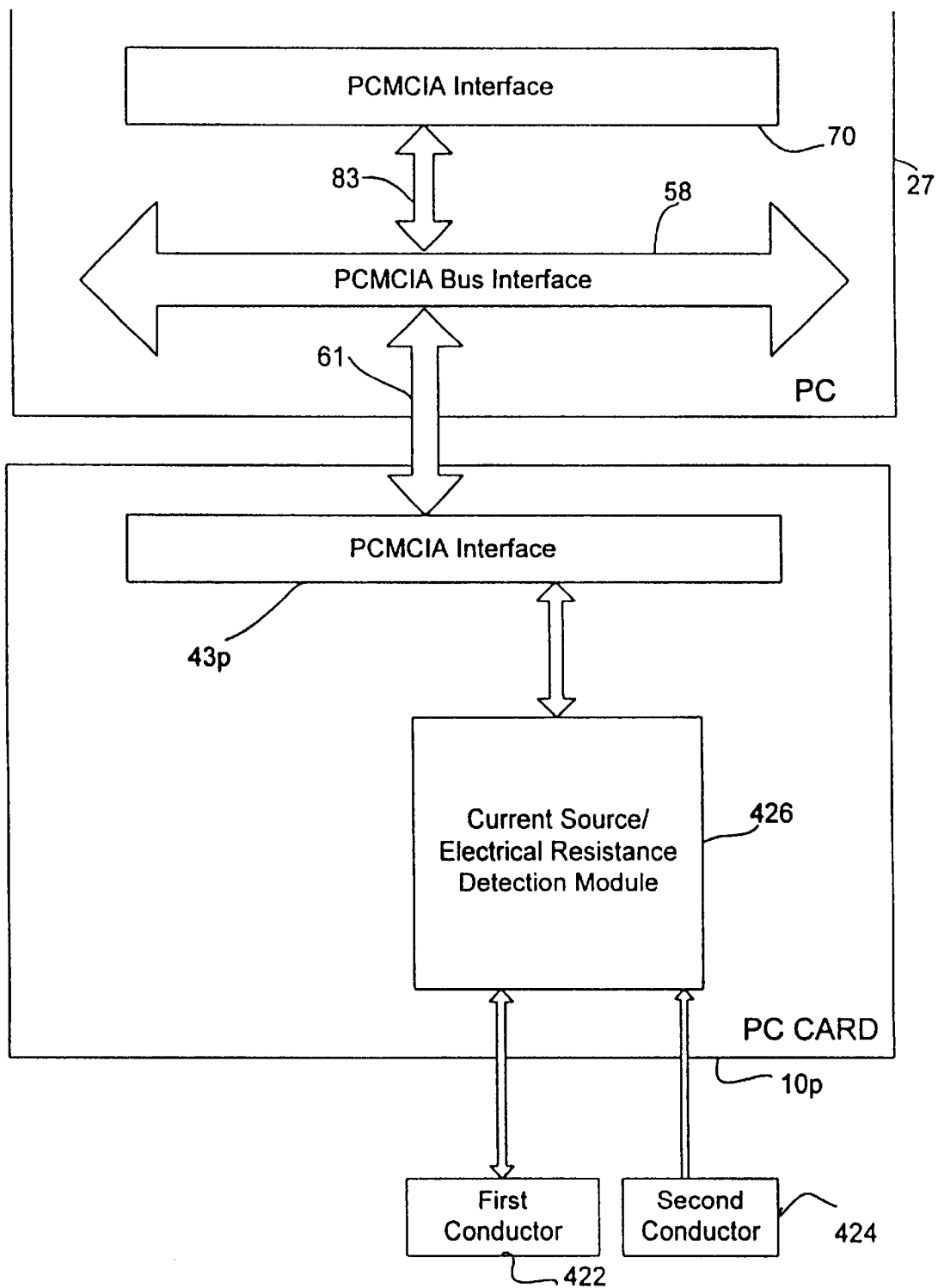
FIG. 23 illustrates a schematic block diagram of a real-time biological data processing PC card for collecting and forwarding on a real-time basis body composition data.

A real-time biological data processing PC card 10*p* for collecting and forwarding on a real-time basis body composition data is illustrated in FIG. 23. A first conductor 422 and a second conductor 424 provide electrical resistance data on a real-time basis to the current source/electrical resistance module 426, which subsequently forwards processed information to the PCMCIA interface 43*p*. The current source/electrical resistance detection module 426 in a preferred embodiment injects an electrical signal into a patient via the first conductor 422, and uses the second detector 424 to determine an electrical resistance of the patient. In modified embodiments, either the current source, the electrical resistance detector, or both, may be disposed within the host personal computer 27. Based upon the measured electrical resistance and the electrical signal injected into the patient, an estimate of a fat composition of the patient is generated and forwarded to the PCMCIA interface 43*p* on a real-time basis.

Figure 24:
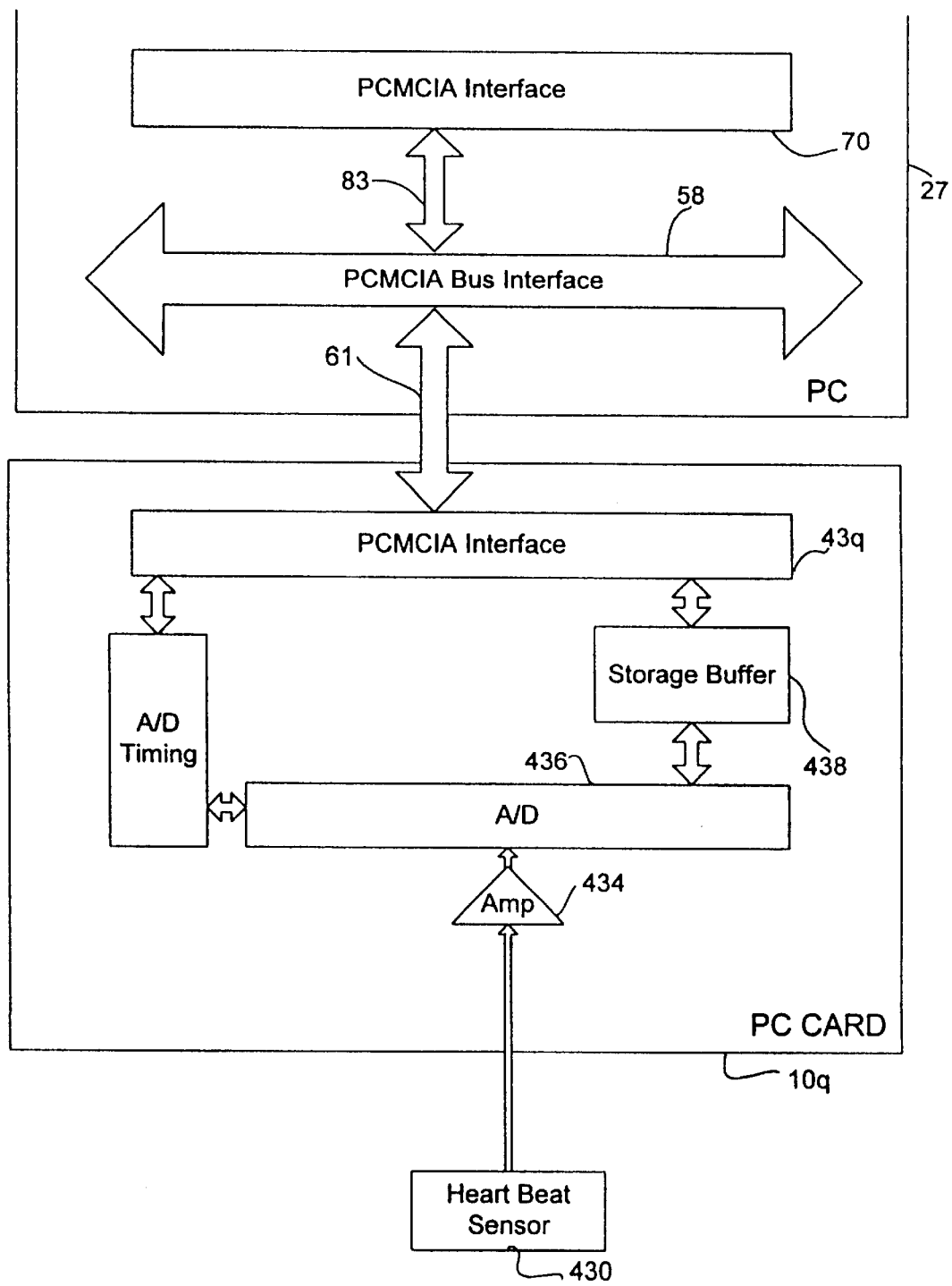
FIG. 24 illustrates a schematic block diagram of a real-time biological data processing PC card for collecting and forwarding on a real-time basis heart beat data.

The PC card 10*q* illustrated in FIG. 24 collects heartbeat information on a real-time basis from a heartbeat sensor 430. The heartbeat information is processed via, an amplifier 434 and an analog-to-digital converter 436, and is passed on a real-time basis to the PCMCIA interface 43*q* via a storage buffer 438. The real-time heartbeat data can be monitored and manipulated on the personal computer 27.

Figure 25:
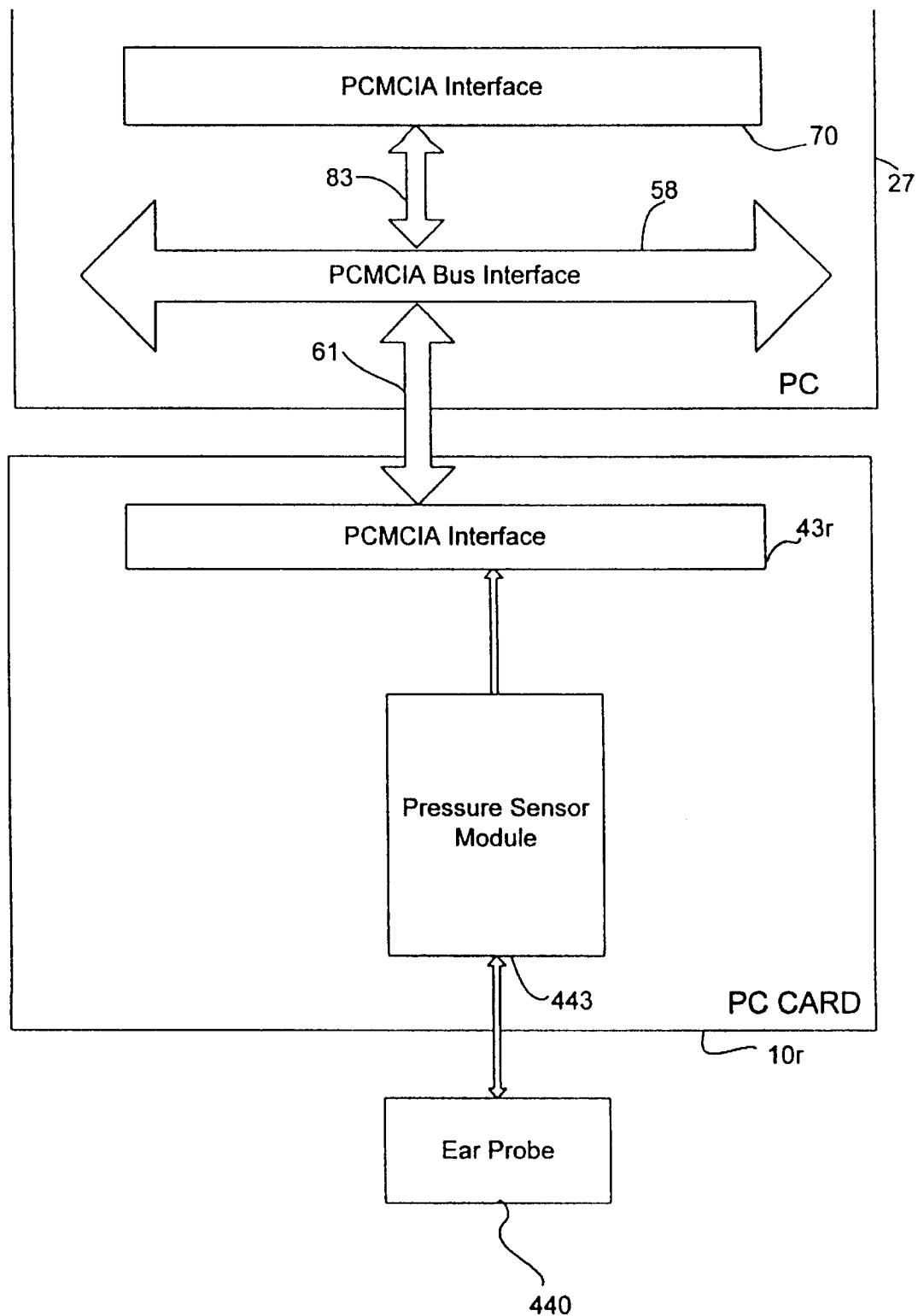
FIG. 25 illustrates a schematic block diagram of a real-time biological data processing PC card for collecting and forwarding on a real-time basis ear-drum pressure data.

The PC card 10*r* of FIG. 25 inputs data on a real-time basis from an ear probe 440 into a pressure sensor module 443, which processes the data and subsequently outputs the processed data to the PCMCIA interface 43*r* on a real-time basis. The EUI probe 440 may comprise a hand-held wand for placement into the ear of a patient. The hand-held wand may comprise mechanical means for measuring the eardrum pressure or, alternatively, may comprise optical means for measuring an eardrum pressure of the patient as is well known in the art.

Figure 26:
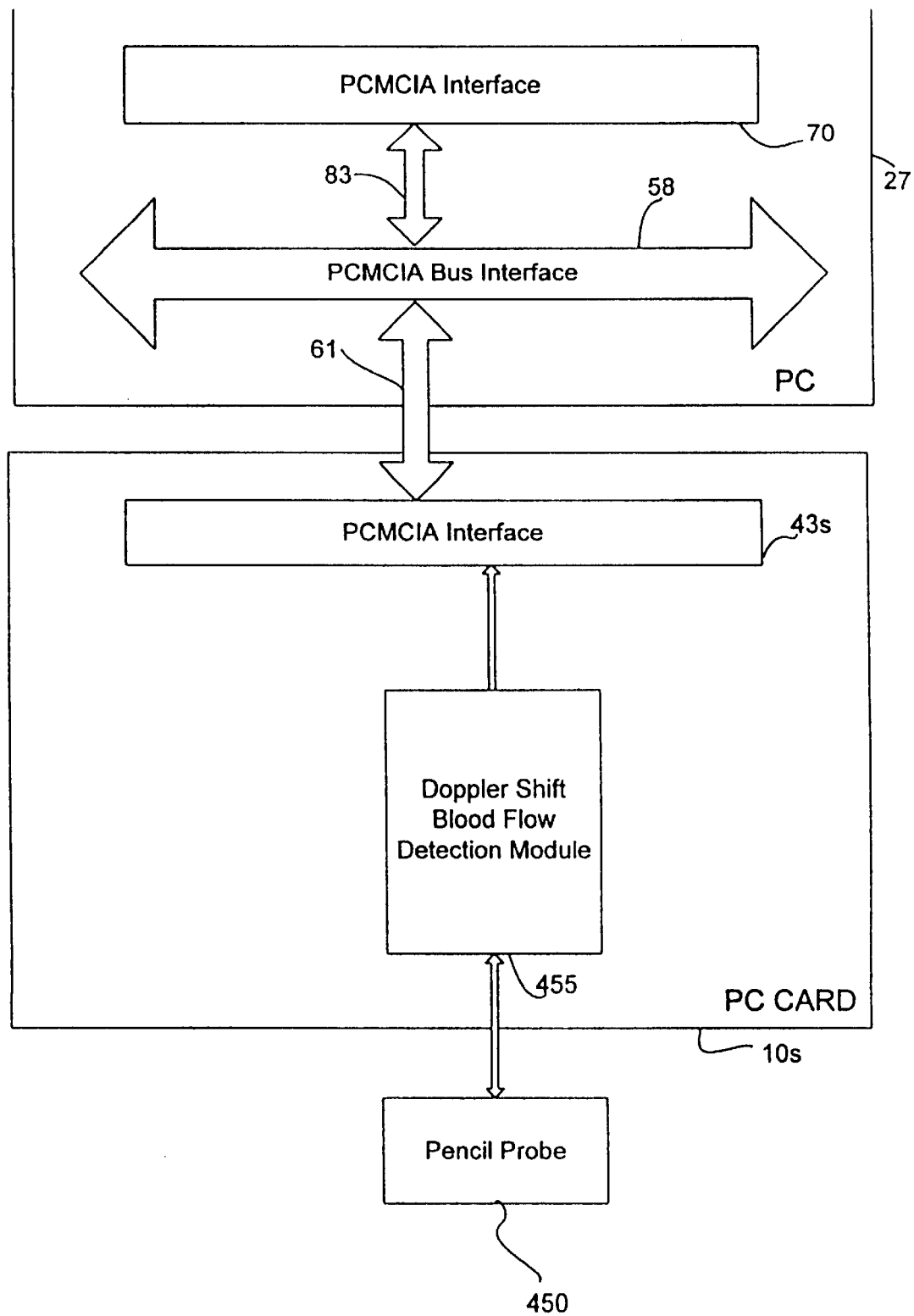
FIG. 26 illustrates a schematic block diagram of a real-time biological data processing PC card for collecting and forwarding on a real-time basis blood flow related data.
Figure 27:
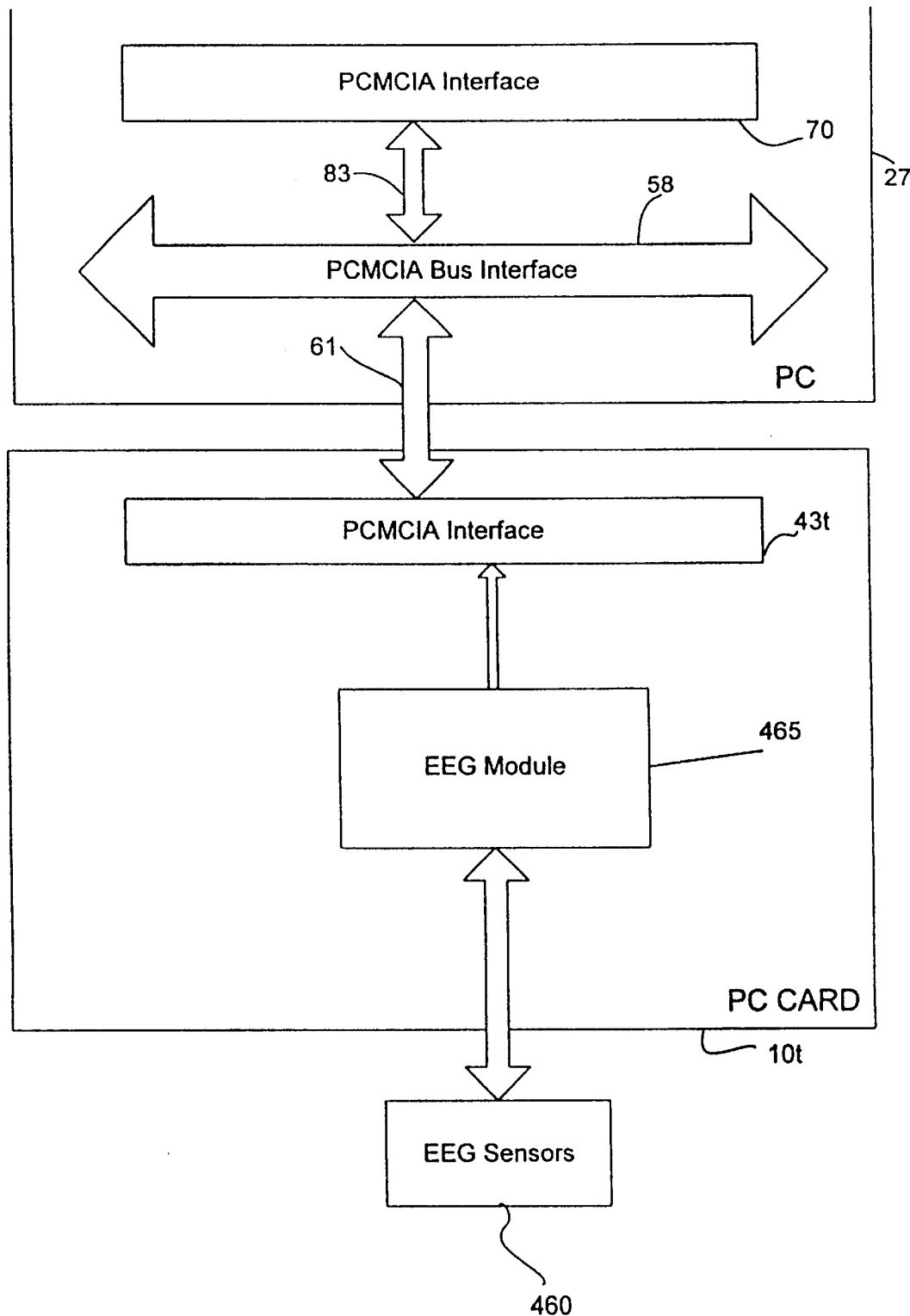
FIG. 27 illustrates a schematic block diagram of a real-time biological data processing PC card for collecting and forwarding on a real-time basis EEG related data.

Turning to FIG. 26, a PC card 10*s* inputs data from a pencil probe 450 into a Doppler shift blood flow detection module 455 on a real-time basis. The pencil probe 450 emits acoustical signals which are used for measuring blood flow as is known in the art. Information from the pencil probe 450 is first processed by the Doppler shift blood flow detection module 455, and is subsequently forwarded on a real-time basis to the PCMCIA interface 43*s* for use by the personal computer 27. The PC card 10*t* in FIG. 27 inputs electrical information from EEG sensors 460 into an EEG module 465 on a real-time basis. The EEG module 465 processes the electrical data and outputs the processed data to a PCMCIA interface 43*t* on a real-time basis for use by the personal computer 27.

Figure 28:
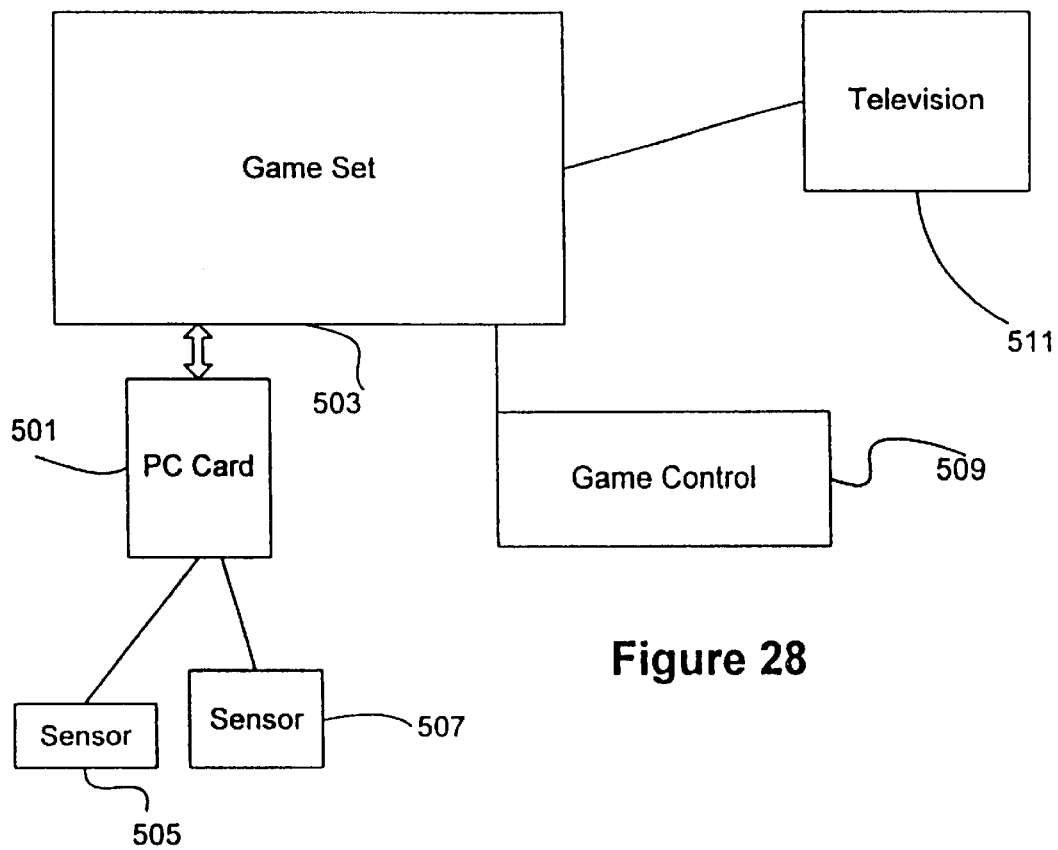
FIG. 28 illustrates a schematic block diagram of a real-time biological data processing PC card for collecting and forwarding on a real-time basis biological data to a game set.

FIG. 28 illustrates a real-time biological data processing PC card 501 connected to a game set 503 for collecting and forwarding on a real-time basis biological data to the game set 503. The biological data is received on a real-time basis into the PC card 501 from one or more sensors 505 and 507. A game control 509 is connected to the game set 503, and a television 511 operates as a monitor. The PC card 501 can be configured similarly to any of the above-described PC cards of the present invention, with an exception of the interface for communicating with the game set 503. The game set 503 may comprise a game set such as Nintendo® or Sega®. If the game set 503 has a Windows CE operating system and a PCMCIA card slot, then the PC card 501 may be virtually identical to any of the above-discussed PC cards of the present invention. If the game set 503 0does not have a PC card slot, then other housings and/or interfaces may be implemented with the PC card 501 to facilitate proper real-time communication between the PC card 501 and the game set 503. One example, compact Flash Cards and compact Flash Card housing(s) maybe used. As another example, proprietary Nintendo® game set digital interfaces may be used with the PC card 501. The game console 509 may be connected to either the game set 503 or the television 511, and may be linked by a conventional cord or by a wireless communication path.

Figure 29:
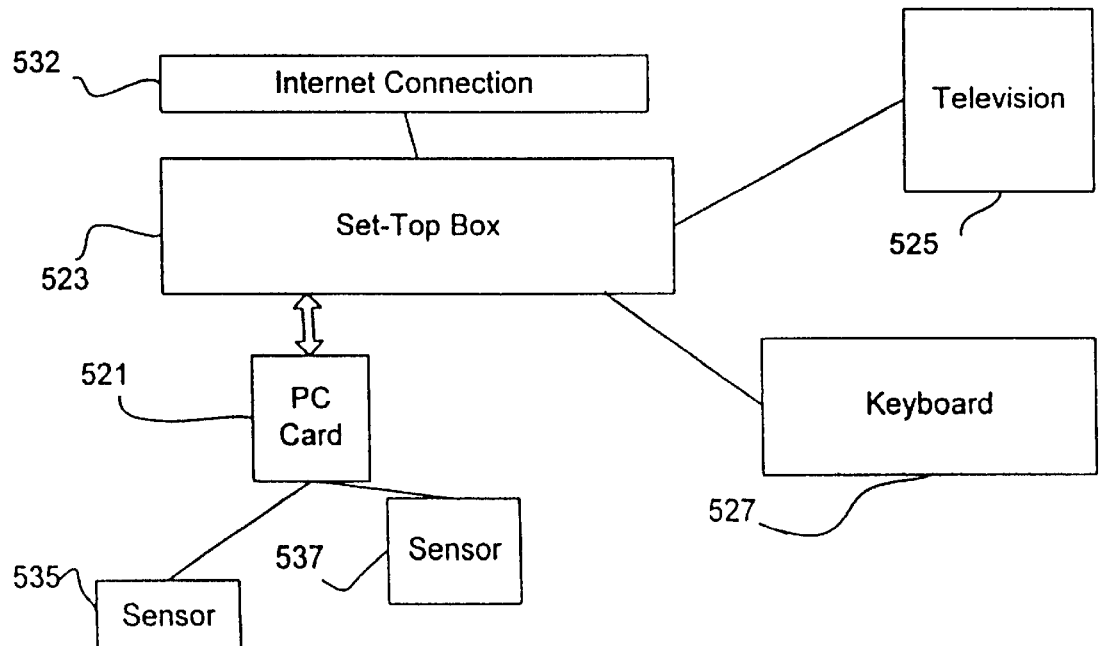
FIG. 29 illustrates a schematic block diagram of a real-time biological data processing PC card for collecting and forwarding on a real-time basis biological data to a set-top box.

FIG. 29 illustrates a real-time biological data processing PC card 521 for collecting and forwarding on a real-time basis biological data to a set-top box 523. The set-top box 523 is connected to a television 525, which operates as a monitor, and is further connected to a keyboard 527. The keyboard 527 may be connected to either the set-top box 523 or the television 525 via a conventional cable or a wireless communication path. In accordance with the illustrated embodiment, the set-top box 523 comprises an Internet connection 532 for facilitating real-time data transfer of biological data from the sensors 535, 537 to one or more receivers on the Internet. The PC card 521 and sensors 535, 537 may comprise any combination of PC cards and sensors discussed in any of the above embodiments. The set-top box 523 can transmit biological data from the sensors 535, 537 on a real-time basis over the Internet to other users, such as a user at a doctor's office or hospital. Additionally, the set-top box 523 can receive biological data on a real-time basis from other users via the Internet connection 532. Information received from other users via the Internet connection 532 can be displayed by the set-top box 523 on the television 525, for example.

Information can be transmitted and received through the Internet connection 532 either on a real-time basis or, alternatively, at predetermined intervals. The set-top box 523 may be configured to automatically dial out and establish an Internet connection, and to transmit or receive real-time biological data over the Internet, at predetermined or user-defined intervals. A patient can conduct tests using one or more sensors, such as the sensors 535 and 537, and at the same time or at a later time, transmit the data to a doctor via the Internet connection 532. In addition to a set-top box 523, Internet telephones, personal computers, wireless Internet computers, network computers or other Internet "appliances" capable of sending real-time data over the Internet may be used. In one embodiment, game sets may be used to transmit or receive the real-time biological data over the Internet.

In modified configurations of the above-described embodiments, some or all of the circuitry and/or components for each of the modules on the personal computer cards can be placed within the host microprocessor system, so long as the card is able to input digital information to the host microprocessor system. Moreover, in other modified configurations circuitry and/or components for each of the modules on the personal computer cards can be placed on the biological data sensors themselves, in addition to or in the alternative to placement of the circuitry and/or components on the host microprocessor system. In embodiments where the signal or signals from the biological data sensor or sensors is simply digitized and forwarded to the host microprocessor system (personal computer, game set, set-top box, etc.) for subsequent processing and interpretation, the signal-conditioning circuitry can comprise the bare-essential elements, such as merely an analog-to-digital converter, for formatting the data from the biological data sensors and forwarding to the host microprocessor system.

In embodiments wherein the host microprocessor system comprises a game set, for example, the personal computer card may have additional initializing data. This may be the case for embodiments wherein other types of host microprocessor systems are used, as well. In some embodiments, the host microprocessor system is loaded with initializing data and instructions, for example, before the personal computer card is loaded into the host microprocessor system. In other embodiments, substantial amounts of data and/or instructions are loaded into the host microprocessor system (or game set, set-top box, etc.) by the personal computer card at the time of insertion of the personal computer card into the host microprocessor system.

In any of the above-described embodiments of the present invention, the personal computer card may comprise a PCMCIA-type card, a card having an interface which is adapted to communicate with a game set, a compact flash card, or any other type of portable card with an interface for transmitting data to a host microprocessor system. An example of a host microprocessor system adapted for accommodating compact flash cards is the Cassiopeia E-10, manufactured by Casio Computer Co. Ltd and described at http://www.casiohpc.com/indes.html.

Although exemplary embodiments of the invention have been shown and described, many other changes, modifications and substitutions, in addition to those set forth in the above paragraphs, may be made by one having ordinary skill in the art without necessarily departing from the spirit and scope of the present invention.

What is claimed is:

1. A portable biological data collection device comprising:
   a biological data receiver for receiving biological data from a biological data sensor for producing a biological data signal;
   an amplifier for amplifying the biological data signal from the biological data receiver to produce an amplified signal;
   an analog-to-digital converter for digitizing the amplified signal to produce a digitized signal; and
   a personal computer card interface for relaying the digitized signal to a host computer on a real-time basis as the biological data is received by the biological data receiver, and for supplying electrical power from the host computer to the amplifier and the analog-to-digital converter.

2. The portable biological data collection device of claim 1 further comprising a personal computer card housing, wherein the biological data receiver, the amplifier, the analog-to-digital converter, and the personal computer card interface are disposed within the personal computer card housing.

3. The portable biological data collection device of claim 1 further comprising an analog-to-digital timing circuit adapted to communicate with the analog-to-digital converter for producing a sampling timing signal, and a storage buffer adapted to receive the digitized signal from the analog-to-digital converter for outputing the digitized signal, wherein the personal computer card interface is further adapted to supply electrical power from the host computer to the analog-to-digital timing circuit and the storage buffer.

4. The portable biological data collection device of claim 3 further comprising a personal computer card housing, wherein the biological data receiver, the amplifier, the analog-to-digital converter, analog-to-digital timing circuit, the storage buffer, and the personal computer card interface are disposed within the personal computer card housing.

5. The portable biological data collection device of claim 4, wherein the personal computer card interface is further adapted to relay designation data to the host computer for allowing the host computer to identify the biological data to be collected.

6. The portable biological data collection device of claim 1, wherein the personal computer card interface is further adapted to relay designation data to the host computer for allowing the host computer to identify the biological data to be collected.

7. The portable biological data collection device of claim 6 further comprising a personal computer card housing, wherein the biological data receiver, the amplifier, the analog-to-digital converter, and the personal computer card interface are disposed within the personal computer card housing.

8. The portable biological data collection device of claim 1, further comprising electrical isolation circuitry disposed between the biological data receiver and the amplifier for electrically isolating a patient from the electrical power.

9. The portable biological data collection device of claim 8 further comprising a personal computer card housing, wherein the biological data receiver, the amplifier, the analog-to-digital converter, the personal computer card interface, and the electrical isolation circuitry are disposed within the personal computer card housing.

10. A portable biological data collection comprising:
    a conductor for collecting biological data from a patient;
    an amplifier for amplifying the biological data from the conductor to produce an amplified signal;
    an analog-to-digital converter for digitizing the amplified signal to produce a digitized signal;
    a personal computer card interface for relaying the digitized signal to a host computer on a real-time basis as the biological data is collected by the conductor, and for supplying electrical power from the host computer to the amplifier and the analog-to-digital converter; and
    electrical isolation circuitry disposed between the conductor and the amplifier for electrically isolating a patient from the electrical power.

11. The portable biological data collection device of claim 10 further comprising a personal computer card housing, wherein the amplifier; the analog-to-digital converter, the personal computer card interface, and the electrical isolation circuitry are disposed within the personal computer card housing.

12. The portable biological data collection device of claim 10 further comprising an analog-to-digital timing circuit providing a sampling timing signal to the analog-to-digital converter, and a storage buffer for receiving and storing the digitized signal from the analog-to-digital converter, wherein the personal computer card interface supplies electrical power from the host computer to the analog-to-digital timing circuit and the storage buffer.

13. The portable biological data collection device of claim 12 further comprising a personal computer card housing, wherein the amplifier, the analog-to-digital converter, analog-to-digital timing circuit, the storage buffer, the personal computer card interface, and the electrical isolation circuitry are disposed within the personal computer card housing.

14. A portable biological data collection comprising:
    a pressure sensor for receiving a pressure signal from a patient and converting the pressure signal into an electrical signal;
    an amplifier for and amplifying the electrical signal from the pressure sensor to produce an amplified signal;

an analog-to-digital converter for digitizing the amplified signal to produce a digitized signal; and a personal computer card interface for relaying the digitized signal to a host computer on a real-time basis as the pressure signal is collected by the pressure sensor, and for supplying electrical power from the host computer to the amplifier and the analog-to-digital converter.

15. The portable biological data collection device of claim 14 further comprising a personal computer card housing, wherein the pressure sensor, the amplifier, the analog-to-digital converter, and the personal computer card interface are disposed within the personal computer card housing.

16. The portable biological data collection device of claim 14 further comprising an analog-to-digital timing circuit for providing a sampling timing signal to the analog-to-digital converter, and a storage buffer for receiving and storing the digitized signal from the analog-to-digital converter, wherein the personal computer card interface supplies electrical power from the host computer to the analog-to-digital timing circuit and the storage buffer.

17. The portable biological data collection device of claim 16 further comprising a personal computer card housing, wherein the pressure sensor, the amplifier, the analog-to-digital converter, analog-to-digital timing circuit, the storage buffer, and the personal computer card interface are disposed within the personal computer card housing.

18. A portable biological data collection device comprising:

a biological data receiver for receiving biological data from a biological data sensor and producing a biological data signal;

an amplifier for amplifying the biological data signal from the biological data receiver to produce an amplified signal;

an analog-to-digital converter for digitizing the amplified signal to produce a digitized signal; and a personal computer card interface connectable to an external port of a host computer for relaying the digitized signal to the host computer on a real-time basis as the biological data is received by the biological data receiver, and for supplying electrical power from the host computer to the amplifier and the analog-to-digital converter.

19. The portable biological data collection device of claim 18 further comprising a personal computer card housing, wherein the biological data receiver, the amplifier, the analog-to-digital converter, and the personal computer card interface are disposed within the personal computer card housing.

20. A biological data collection system comprising:

a host computer comprising an external computer card port;

a portable biological data collection device comprising:
a personal computer card housing;
a biological data receiver disposed within the personal computer card housing for receiving biological data from a biological data sensor and producing a biological data signal;
an amplifier disposed within the personal computer card housing for amplifying the biological data signal from the biological data receiver to produce an amplified signal;
an analog-to-digital converter disposed within the personal computer card housing for digitizing the amplified signal to produce a digitized signal; and
a personal computer card interface disposed within the personal computer card housing and connectable to the external computer card port of a host computer to supply electrical power from the host computer to the amplifier and the analog-to-digital converter; and software installed in the host computer for allowing the personal computer card interface to relay the digitized signal to the host computer on a real-time basis as the biological data is received by the biological data receiver.

21. The portable biological data collection device of claim 20, wherein the portable biological data collection device further comprises:

an analog-to-digital timing circuit disposed within the personal computer card housing for providing a sampling timing signal to the analog-to-digital converter; and a storage buffer disposed within the personal computer card housing storage the digitized signal from the analog-to-digital converter;

wherein the personal computer card interface supplies electrical power from the host computer to the analog-to-digital timing circuit and the storage buffer.

22. A method for converting a host computer into a biological data collection system comprising:

connecting a personal computer card interface of a portable biological data collection device with an external personal computer card port of the host computer;

relaying designation data from the personal computer card interface to the host computer for allowing the host computer to identify a type of biological data to be collected;

receiving biological data of a patient to a biological data receiver of the portable biological data collection device for producing a biological data signal, wherein the biological data corresponds to the type of biological data identified by the host computer;

amplifying the biological data signal with an amplifier of the portable biological data collection device for producing an amplified signal, wherein the amplifier receives power from the host computer through the personal computer card interface;

digitizing the amplified signal with the analog-to-digital converter of the portable biological data collection device for producing a digitized signal, wherein the analog-to-digital converter receives power from the host computer through the personal computer card interface; and relaying the digitized signal from the personal computer card interface to the host computer on a real-time basis as the biological data is received by the biological data receiver.

23. A method for converting a host computer into a biological data collection system comprising:

inserting a biological data processing personal computer card into an external computer card port of the host computer;

relaying power from the host computer to the biological data processing personal computer card through the external computer card port of the host computer;

directing the host computer to identify the type of biological data processing personal computer card inserted into the external computer card port;

directing the host computer to collect biological data from the biological data processing personal computer card on a real-time basis as the biological data is received and processed by the biological data processing personal computer card, wherein the receiving and processing by the biological data processing personal computer card comprises:

receiving the biological data from a patient to a biological data receiver of the biological data processing personal computer card, wherein the biological data corresponds to the type of biological data identified by the host computer;

amplifying the biological data with an amplifier of the biological data processing personal computer card;

digitizing the amplified biological data with the analog-to-digital converter of the biological data processing personal computer card; and relaying the amplified, digitized biological data to a personal computer card interface of the biological data processing personal computer card; and displaying the biological data as it is collected from the biological data processing personal computer card on the host computer.

24. The method of claim 23, wherein the step of directing the host computer to identify the type of biological data processing personal computer card inserted into the external computer card port comprises relaying designation data from the biological data processing personal computer card.

25. The method of claim 23, wherein the step of directing the host computer to identify the type of biological data processing personal computer card inserted into the external computer card port comprises inputting designation data from a user input device in connection with the host computer.

26. A portable biological data collection device comprising:

a biological data receiver housing;

a personal computer card interface housing adapted to mate with an external personal computer card port of a host computer;

a biological data receiver disposed within the biological data receiver housing for receiving biological data from a biological data sensor and producing a biological data signal;

an amplifier disposed within the biological data receiver housing for amplifying the biological data signal from the biological data receiver to produce an amplified signal;

an analog-to-digital converter disposed within the personal computer card interface housing for digitizing the amplified signal to produce a digitized signal; and a personal computer card interface disposed within the personal computer card interface housing for relaying the digitized signal to the host computer on a real-time basis as the biological data is received by the biological data receiver, and supplying electrical power from the host computer to the amplifier and the analog-to-digital converter.

27. The portable biological data collection device of claim 26, wherein the personal computer card interface relays designation data to the host computer for allowing the host computer to identify the biological data to be collected.

28. The portable biological data collection device of claim 27 further comprising:

an analog-to-digital timing circuit disposed within the personal computer card interface housing for providing a sampling timing signal to the analog-to-digital converter; and a storage buffer disposed within the personal computer card interface housing for storing the digitized signal from the analog-to-digital converter;

wherein the personal computer card interface supplies electrical power from the host computer to the analog-to-digital timing circuit and the storage buffer.

29. The portable biological data collection device of claim 26, further comprising electrical isolation circuitry disposed within the biological data receiver housing, and disposed between the biological data receiver and the amplifier for electrically isolating a patient from the electrical power.

30. The portable biological data collection device of claim 29, wherein the personal computer card interface relays designation data to the host computer for allowing the host computer to identify the biological data to be collected.

31. The portable biological data collection device of claim 30 further comprising:

an analog-to-digital timing circuit disposed within the personal computer card interface housing for providing a sampling timing signal to the analog-to-digital converter; and a storage buffer disposed within the personal computer card interface housing for storing the digitized signal from the analog-to-digital converter for outputting the digitized signal;

wherein the personal computer card interface supplies electrical power from the host computer to the analog-to-digital timing circuit and the storage buffer.

32. A portable ECG data collection device comprising:

a plurality of ECG leads adapted to receive ECG data from a patient for producing ECG signals;

electrical isolation circuitry for receiving the ECG signals and producing isolated ECG signals;

an amplifier for amplifying the isolated ECG signals to produce amplified ECG signals;

a filter for filtering the amplified ECG signals to produce filtered ECG signals:

an analog-to-digital converter for and digitizing the filtered ECG signals to produce digitized ECG signals;

an analog-to-digital timing circuit for providing a sampling timing signal to the analog-to-digital converter;

a storage buffer for storing the digitized ECG signals; and a personal computer card interface for relaying the digitized ECG signal from the storage buffer to a host computer on a real-time basis as the ECG data is received by the plurality of ECG leads, and supplying electrical power from the host computer to the electrical isolation circuitry, the amplifier, the filter, the analog-to-digital converter, the analog-to-digital timing circuit, and the storage buffer.

33. The portable ECG data collection device of claim 32 further comprising a personal computer card housing, wherein the electrical isolation circuitry, the amplifier, the filter, the analog-to-digital converter, the analog-to-digital timing circuit, the storage buffer, and the personal computer card interface are disposed within the personal computer card housing.

34. The portable ECG data collection device of claim 32, further comprising a defibrillator protector for providing electrical protection to the portable biological collection device and receiving the ECG signals from the plurality of ECG leads.

35. The portable ECG data collection device of claim 34, further comprising a noise reducer for receiving the ECG signals from the defibrillator protector and reducing signal noise, wherein the personal computer card interface supplies electrical power from the host computer to the noise reducer.

36. The portable ECG data collection device of claim 35 further comprising a personal computer card housing, wherein the defibrillator protector, the noise reducer, the electrical isolation circuitry, the amplifier, the filter, the analog-to-digital converter, the analog-to-digital timing circuit, the storage buffer, and the personal computer card interface are disposed within the personal computer card housing.

* * * * *

UNITED STATES PATENT AND TRADEMARK OFFICE
CERTIFICATE OF CORRECTION

PATENT NO. : 6,712,762 B1
DATED : March 30, 2004
INVENTOR(S) : Lichter et al.

It is certified that error appears in the above-identified patent and that said Letters Patent is hereby corrected as shown below:

Column 24,
Line 6, add:
-- 37. The portable biological data collection device of claim 26 further
comprising:
an analog-to-digital timing circuit disposed within the personal computer
card interface housing for providing a sampling timing signal to
analog-to-digital converter; and a storage buffer disposed within the personal computer card interface
housing for storing the digitized signal from the analog-to-digital
converter, wherein the personal computer card interface supplies electrical power
from the host computer to the analog-to-digital timing circuit and
the storage buffer. --.

Signed and Sealed this

Twenty-seventh Day of December, 2005

JON W. DUDAS
*Director of the United States Patent and Trademark Office*